(12) United States Patent
Barsanti et al.

(10) Patent No.: US 12,269,820 B2
(45) Date of Patent: Apr. 8, 2025

(54) PIPERAZINE SUBSTITUTED INDAZOLE COMPOUNDS AS INHIBITORS OF PARG

(71) Applicant: IDEAYA BIOSCIENCES, INC., South San Francisco, CA (US)

(72) Inventors: Paul A. Barsanti, South San Francisco, CA (US); Michael Patrick Dillon, South San Francisco, CA (US); Firoz Ali Jaipuri, South San Francisco, CA (US); Ying-Zi Xu, South San Francisco, CA (US); Xin Linghu, South San Francisco, CA (US)

(73) Assignee: IDEAYA Biosciences, Inc., South San Francisco, CA (US)

( * ) Notice: Subject to any disclaimer, the term of this patent is extended or adjusted under 35 U.S.C. 154(b) by 78 days.

(21) Appl. No.: 18/188,278

(22) Filed: Mar. 22, 2023

(65) Prior Publication Data
US 2023/0303556 A1    Sep. 28, 2023

Related U.S. Application Data

(60) Provisional application No. 63/322,994, filed on Mar. 23, 2022.

(51) Int. Cl.
*C07D 417/14* (2006.01)
*A61P 35/00* (2006.01)

(52) U.S. Cl.
CPC ............ *C07D 417/14* (2013.01); *A61P 35/00* (2018.01)

(58) Field of Classification Search
CPC ............................... C07D 417/14; A61P 35/00
See application file for complete search history.

(56) References Cited

U.S. PATENT DOCUMENTS

| | | | |
|---|---|---|---|
| 4,429,126 A | 1/1984 | Ueda et al. |
| 5,472,961 A | 12/1995 | Gottschlich et al. |
| 7,582,652 B2 | 9/2009 | Bonjouklian et al. |
| 7,994,202 B2 | 8/2011 | Atobe et al. |
| 10,239,843 B2 | 3/2019 | McGonagle et al. |
| 10,508,086 B2 | 12/2019 | McGonagle et al. |
| 10,995,073 B2 | 5/2021 | McGonagle et al. |
| 12,129,236 B2 | 10/2024 | McGonagle et al. |
| 2007/0049593 A1 | 3/2007 | Oka et al. |
| 2007/0219195 A1 | 9/2007 | Goldstein et al. |
| 2009/0149417 A1 | 6/2009 | Ossovskaya et al. |
| 2012/0329784 A1 | 12/2012 | Lallander et al. |
| 2014/0171363 A1 | 6/2014 | Barnes et al. |
| 2018/0016242 A1 | 1/2018 | McGonagle et al. |
| 2018/0194738 A1 | 7/2018 | McGonagle et al. |
| 2020/0165208 A1 | 5/2020 | McGonagle et al. |
| 2021/0380539 A1 | 12/2021 | McGonagle et al. |
| 2022/0202821 A1 | 6/2022 | Tainer et al. |
| 2022/0389003 A1 | 12/2022 | Sutton, Jr. et al. |
| 2023/0272485 A1 | 8/2023 | Hassig et al. |

FOREIGN PATENT DOCUMENTS

| | | |
|---|---|---|
| CN | 101429191 A | 5/2009 |
| DE | 19927415 A1 | 12/2000 |
| EP | 1719773 A1 | 11/2006 |
| WO | WO-200076966 A2 | 12/2000 |
| WO | WO-200102369 A2 | 1/2001 |
| WO | WO-200116108 A2 | 3/2001 |
| WO | WO-2003068743 A1 | 8/2003 |
| WO | WO-2004083204 A1 | 9/2004 |
| WO | WO-2005030212 A1 | 4/2005 |
| WO | WO-2005092890 A1 | 10/2005 |
| WO | WO-2007014226 A2 | 2/2007 |
| WO | WO-2007087488 A2 | 8/2007 |

(Continued)

OTHER PUBLICATIONS

Gaikwad, Digambar D., et al. "Synthesis of Indazole Motifs and Their Medicinal Importance: An Overview." European Journal of Medicinal Chemistry, vol. 90, Jan. 2015, pp. 707-731, doi:10.1016/j.ejmech.2014.11.029. (Year: 2015).*
Rizwan, Muhammad, et al. "A Comprehensive Review on the Synthesis of Substituted Piperazine and Its Novel Bio-Medicinal Applications." Chemistry of Inorganic Materials, vol. 2, Apr. 2024, p. 100041, doi:10.1016/j.cinorg.2024.100041. (Year: 2024).*
Belikov, V. G. "Pharmaceutical Chemistry: Manual", Moscow: MEDpress-inform, 2007, pp. 27-29.
Chen, Shih-Hsun et al., "Targeting dePARylation selectively suppresses DNA repair-defective and PARP inhibitor-resistant malignancies," Sci. Adv. (Apr. 10, 2019) 5:eaav4340, 14 pages.

(Continued)

*Primary Examiner* — Kortney L. Klinkel
*Assistant Examiner* — Donna M Nestor
(74) *Attorney, Agent, or Firm* — Mintz Levin Cohn Ferris Glovsky and Popeo PC

(57) ABSTRACT

Provided herein are compounds of Formula (I):

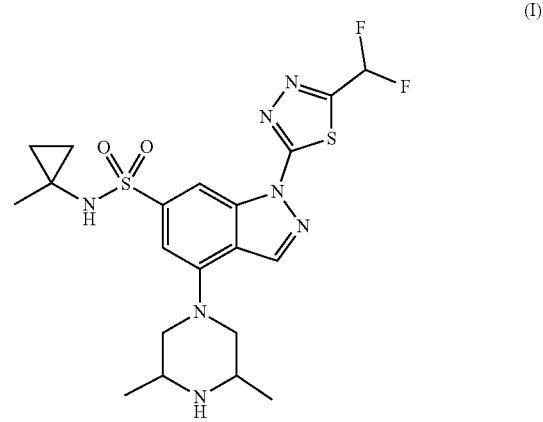

or a pharmaceutically acceptable salt thereof. The provided compounds are useful Poly ADP-ribose glycohydrolase (PARG) inhibitors. Additional utilities and advantages are described herein.

12 Claims, 3 Drawing Sheets

(56) References Cited

FOREIGN PATENT DOCUMENTS

| WO | WO-2009047255 A1 | 4/2009 | | |
|---|---|---|---|---|
| WO | WO-2011140325 A1 | 11/2011 | | |
| WO | WO-2011140442 A1 | 11/2011 | | |
| WO | WO-2012035078 A1 | 3/2012 | | |
| WO | WO-2012080284 A2 | 6/2012 | | |
| WO | WO-2012089721 A1 | 7/2012 | | |
| WO | WO-2012160464 A1 | 12/2012 | | |
| WO | WO-2013027168 A1 | 2/2013 | | |
| WO | WO-2013067300 A1 | 5/2013 | | |
| WO | WO-2014026327 A1 | 2/2014 | | |
| WO | WO-2014028589 A2 | 2/2014 | | |
| WO | WO-2014/106019 A2 | 7/2014 | | |
| WO | 2015/153683 A1 | 8/2015 | | |
| WO | 2015/153683 A8 | 8/2015 | | |
| WO | WO-2015121209 A1 | 8/2015 | | |
| WO | 2016/092326 A1 | 6/2016 | | |
| WO | WO-2016097749 A1 | 6/2016 | | |
| WO | 2018/093696 A1 | 5/2018 | | |
| WO | WO-2021055744 A1 * | 3/2021 | ........... | A61K 31/433 |
| WO | 2023/057389 A1 | 4/2023 | | |
| WO | 2023/057394 A1 | 4/2023 | | |
| WO | 2023/154913 A1 | 8/2023 | | |
| WO | 2023/183850 A1 | 9/2023 | | |
| WO | 2024/002284 A1 | 1/2024 | | |
| WO | 2024/074497 A1 | 4/2024 | | |
| WO | 2024/148280 A1 | 7/2024 | | |
| WO | 2024/173453 A1 | 8/2024 | | |
| WO | 2024/173514 A1 | 8/2024 | | |
| WO | 2024/173524 A1 | 8/2024 | | |
| WO | 2024/173530 A1 | 8/2024 | | |

OTHER PUBLICATIONS

Durnov, L. A. D urnov et al., "Pediatric Oncology", Moscow: Medicine, 2002, p. 139.
Guidelines for Pre-Clinical Studies of Drugs, Part 1, Moscow: Grif & K, 2012, 944 pages, see pp. 509-524, 566-575.
International Search Report and Written Opinion for International Application No. PCT/US2020/051486, mailed Mar. 5, 2021, 9 pages.
International Search Report and Written Opinion for International Application No. PCT/US2023/064825, mailed Jun. 30, 2023, 12 pages.
International Search Report and Written Opinion for International Application No. PCT/US2024/010508, mailed Apr. 11, 2024, 14 pages.
International Search Report and Written Opinion for International Application No. PCT/US2024/015669, mailed May 13, 2024, 12 pages.
International Search Report and Written Opinion for International Application No. PCT/US2024/015758, mailed May 28, 2024, 12 pages.
International Search Report and Written Opinion for International Application No. PCT/US2024/015746, mailed May 29, 2024, 14 pages.
International Search Report and Written Opinion for International Application No. PCT/US2024/022979, mailed Jul. 5, 2024, 19 pages.
International Search Report and Written Opinion for International Application No. PCT/US2024/015767, mailed Jul. 17, 2024, 13 pages.
Keung, Man Yee T. et al. "PARP Inhibitors as a Therapeutic Agent for Homologous Recombination Deficiency in Breast Cancers," *Journal of Clinical Medicine*, (Mar. 30, 2019); 8(435), pp. 1-24.
Kholodov, L. E., et al., "Clinical Pharmacokinetics", Moscow: Medicine, 1985, pp. 83-98, 134-138, 160, 378-380. [See, concise statement.].
Kümmerer, K, Pharmaceuticals in the environment, Annual Review of Environment and Resources, 2010, V. 35, pp. 57-75, doi: 10.1146/annurev-environ-052809-161223.
Li, He et al., "PARP inhibitor resitrance: the underlying mechanisms and clinical implications," *Molecular Cancer*, (Jun. 20, 2020); 19(107), pp. 1-16.
Ouyang, Guang et al., "Synthesis and Antitumor Evaluation of Novel 5-Hydrosulfonyl-1 H-benzol[d]imidazole-2(3H)-one Derivatives," *Molecules* (Apr. 20, 2016); 21(516):1-11.
Sergeev, P. V., "Short Course in Molecular Pharmacology" Moscow, 1975, p. 10. [See, concise statement.].
Slade, Dea, "PARP and PARG inhibitors in cancer treatment," *Genes & Development* (Mar. 1, 2020) 34(5-6):360-394.
Aldlab Chemicals Building Blocks (Nov. 2, 2014), Order No. Cat. AX103678857, see CHEMCATS Acc. No. 2132286836 for the compound having CAS Reg. No. 1411077-15-0; 18 pages.
Amé, Jean-Christophe, "Radiation-induced mitotic catastrophe in PARG-deficient cells," Journal of Cell Science (Accepted Feb. 24, 2009); 122:1990-2002.
Barber, Louise J. et al., "Secondary mutations in BRCA2 associated with clinical resistance to a PARP inhibitor," J Pathol (2013; accepted Oct. 24, 2012); 229:442-429.
Blen, Christian et al., "The Ups and Downs of Tannins as Inhibitors of Poly(ADP-Ribose)glycohydrolase," Molecules (Feb. 22, 2011) 16:1854-1877.
Caiafa, Paola et al., "Epigenetics: poly(ADP-ribosyl)ation of PARP-1 regulates genomic methylation patterns," The FASEB Journal (Mar. 2009; accepted for publication Oct. 23, 2008); 23:672-678.
Chang, Yu Mi et al., "Petasis reaction of activated quinolone and isoquinoline with various boronic acids," Tetrahedron Letters (Mar. 2, 2005); 46:3053-3056.
Curtin, Nicola et al., "Therapeutic Applications of PARP Inhibitors: Anticancer Therapy and Beyond," Mol Aspects Med. (Dec. 2013; available in PMC Dec. 1, 2014); 34(6): .doi:10.106/j.mam.2013.01. 006 (71 pages).
Dahl, Markus et al., "Fine-Tuning of Smad Protein Function by Poly(ADP-Ribose) Polymerases and Poly(ADP-Ribose) Glycohydrolase during Transforming Growth Factor β Signaling," Plos One (Aug. 18, 2014); 9(8):e103651 (19 pages).
Drost, R. et al., "Opportunities and hurdles in the treatment of BRCA1-related breast cancer," Oncogene (2014; published online Aug. 19, 2013) 33:3753-3763.
Erdélyi, Katalin et al., "Dual role of poly(ADP-ribose) glycohydrolase in the regulation of cell death in oxidatively stressed A549 cells," Faseb J. (Oct. 2009; accepted Jun. 4, 2009); 23(10):3553-3563.
Fathers, Catherine et al., "Inhibition of poly(ADP-ribose) glycohydrolase (PARG) specifically kills BRCA2-deficient tumor cells," Cell Cycle (Mar. 1, 2012); 11(5):990-997.
Fisher, Anna E. O. et al., "Poly(ADP-Ribose) Polymerase 1 Accelerates Single-Strand Break Repair in Concert with Poly(ADP-Ribose) Glycohydrolase," Molecular and Cellular Biology (Aug. 2007; published ahead of print Jun. 4, 2007); 27(15):5597-5604.
Frizzell, Kristine M et al., "Global Analysis of Transcriptional Regulation by Poly(ADP-ribose) Polymerase-1 and Poly(ADP-ribose) Glycohydrolase in MCF-7 Human Breast Cancer Cells," Journal of Biological Chemistry (Dec. 4, 2009); 284(49):33926-33938.
Fujihara, H. et al., "Poly(ADP-ribose) Glycohydrolase Deficiency Sensitizes Mouse ES Cells to DNA Damaging Agents," Current Cancer Drug Targets (Accepted Sep. 17, 2009); 9:953-962.
Guastafierro, Tiziana et al., "ADP-ribose polymer depletion leads to nuclear Ctcf re-localization and chromatin rearrangement," Biochem J. (2013; published as BJ Immediate publication Nov. 2, 2012); 449:623-630.
International Search Report and Written Opinion, mailed on Feb. 23, 2016 corresponding to International Patent Application No. PCT/GB2015/053883 filed on Dec. 11, 2015, 17 pages.
International Search Report mailed on Feb. 4, 2016 corresponding to International Patent Application No. PCT/GB2015/054064 filed on Dec. 17, 2015, 6 pages.
International Search Report and Written Opinion for International Application No. PCT/US2020/051486, mailed Mar. 5, 2021, 3 pages.
Ji, Y et al., "Poly(ADP-ribosyl)ation of heterogeneous nuclear ribonucleaoproteins modulates splicing," Nucleic Acids Research (published online Apr. 3, 2009); 37(11):3501-3513.

(56) References Cited

OTHER PUBLICATIONS

Le May, Nicolas et al., "Poly(ADP-Ribose) Glycohydrolase Regulates Retinoic Acid Receptor-Mediated Gene Expression," Molecular Cell (Dec. 14, 2012); 48:785-798.
Mashimo, Masato et al., "Structure and function of the ARH family of ADP-ribose-acceptor hydrolases," DNA Repair (Mast). (Nov. 2014; available in PMC Nov. 1, 2015); 0:88-94. Doi:10.1016/j.dnarep.2014.03.005; 19 pages.
Milbury et al., Clinical and analytical validation of FoundationOne® CDX, a comprehensive genomic profiling assay for tumors, PLOS One, 2022, 17(3), pp. 1-37.
Mortusewicz, Oliver et al., "PARG is recruited to DNA damage sites through poly(ADP-ribose)- and PCNA-dependent mechanisms," Nucleic Acids Research (Mar. 11, 2011); 39(12):5045-5056.
Nakadate, Yusuke et al., "Silencing of poly(ADP-ribose) glycohydrolase sensitizes lung cancer cells to radiation through the abrogation of DNA damage checkpoint," Biochemical and Biophysical Research Communications (available online Nov. 6, 2013); 441:793-798.
Osmialowski, Borys et al., "2-Acylamino- and 2,4-Bis(acylamino)pyrimidines as Supramolecular Synthons Analyzed by Multiple Noncovalent Interactions. DFT, X-ray Diffraction, and NMR Spectral Studies," The Journal of Organic Chemistry (Nov. 2, 2012); 77:9609-9619.
Peng, Chin-Tzu et al., "The Synthesis of Some 6-N-Substituted Amido Derivatives of 4,6-Diaminquinaldine and a Study of their in vitro Antibacterial Activity," Journal of the American Chemical Society (Jan. 1, 1956); 78:3703-3708.
Registry No. 708996-44-5, 1H-Benzimidazole-5sulfonamide, N-cycloprpyl-2, 3-dihydro-2-oxo, Jul. 13, 2004, 1 page.
Registry No. 1146895-94-4, 1H-Benzimidazole-5-sulfonamide, N-cyclopropyl-2, 3-dihydro-1, 3-dimethyl-2-oxo, May 15, 2009, 3 pages.
Registry No. 1709660-65-0, 6-Quinolinesulfonamide, 2-amino-N-(1-methylcyclopropyl)-. EPO Data, entered STN: May 21, 2015.
Registry No. 1709761-66-9, 6-Quinolinesulfonamide, 2-(thylamino)-N-(1-methylcycloprpyl)- , EPO Data, entered STN: May 21, 2015.
Registry No. 1776414-48-2, 7-Quinolinesulfonamide, 1,2,3,4,-tetrahydro-N-(1-methylcycloprpyl)-, EPO Data, entered STN: Jun. 9, 2015.
Registry No. 1776626-70-0, 6-Quinolinesulfonamide, 2-(methylamino)-N-(1-methylcyclopropyl)-, EPO Data, entered STN: Jun. 9, 2015.
Registry No. 1776710-34-9, 6-Quinolinesolfonamide, 1.2.3.4.-tetrahyrdo-N-(1-methylcycloprophyl, EPO Data, entered STN: Jun. 9, 2015.
Registry No. 1777097-79-6, 6-Quinolinesulfonamide, 2-chloro-N-(1-methycyclopropyl)-, EPO Data, entered STN: Jun. 10, 2015.
Rörsch, Florian et al., Structure-Activity Relationship of Nonacidic Quinazolinone Inhibitors of Human Microsomal Prostaglandin Synthase 1 (mPGES 1); Journal of Medicinal Chemistry (Apr. 26, 2012); 55(8):3792-3803.
Shirai, H. et al., "PARG dysfunction enhances DNA double strand break formation in S-phase after alkylation DNA damage and augments different cell death pathways," Cell Death and Disease (accepted Mar. 1, 2013); 4:e656; doi:10.1038/cddis.2013.133; 10 pages.
Shirai, Hidenori et al., "Parg deficiency confers radio-sensitization through enhanced cell death in mouse ES cells exposed to various forms of ionizing radiation," Biochemical and Biophysical Research Communications (available online Apr. 23, 2013); 435:100-106.
Substance Record for SID 105027706 Pubchem (Feb. 22, 2011) NCBI XP55244192; 6 pages.
Substance Record for SID 49925576 Pubchem (Jul. 10, 2008) NCBI XP55244188; 6 pages.
Sun, Yanyan et al., "Tannic acid, an inhibitor of poly(ADP-ribose) glycohydrolase, sensitizes ovarian carcinoma cells to cisplatin," Anti-Cancer Drugs (Revised form accepted May 23, 2012) 23(9):979-990.
Tani, Junichi et al., "Studies on biologically Active Halogenated Compounds. II. Chemical Modifications of 6-Amino-2-fluoromethyl-3-(o-tolyl)-4(3H)-quinazolinone and the CNS Depressant Activities of Related Compounds," Chem. Pharm. Bull. (Nov. 1, 1979); 27(11):2675-2687.
UK Search Report dated Oct. 1, 2015 corresponding to priority application, GB1422771.4 filed on Dec. 19, 2014, 5 pages.
UK Search Report dated Oct. 5, 2015 corresponding to priority application, GB1422098.2 filed on Dec. 12, 2014, 6 pages.
Written Opinion mailed on Feb. 4, 2016 corresponding to International Patent Application No. PCT/GB2015/054064 filed on Dec. 17, 2015, 7 pages.
Zhou, Yiran et al., "Enhanced DNA Accessibility and Increased DNA Damage Induced by the Absence of Poly(ADP-ribose) Hydrolysis," Biochemistry (published on Web Jul. 23, 2010); 49(34):7360-7366.
Zhou, Yiran et al., "Synergistic cytotoxicity of N-methyl-N'-nitro-N-nitrosoguanidine and absence of poly(ADP-ribose) glycohydrolase involves chromatin decondensation," International Journal of Oncology (accepted Feb. 11, 2011); 39:121-127.
U.S. Appl. No. 18/889,613, filed Sep. 19, 2024, McGonagle et al.

\* cited by examiner

PIPERAZINE SUBSTITUTED INDAZOLE COMPOUNDS AS INHIBITORS OF PARG

CROSS-REFERENCES TO RELATED APPLICATIONS

This application claims the benefit of priority under 35 U.S.C § 119(e) to U.S. Provisional Application Ser. No. 63/322,994 filed Mar. 23, 2022, the disclosure of which is incorporated herein by reference in its entirety.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Cancer is caused by uncontrolled and unregulated cellular proliferation. The consequence of this often-rapid proliferation is a high level of oxidative stress within the tumor which damages DNA and leads to a much-increased mutation rate. Tumor cells therefore engage and rely heavily upon DNA damage repair mechanisms.

Single-strand breaks (SSBs) are the most common type of lesion arising in cells and PARG (Poly ADP-ribose glycohydrolase) together with PARP (poly ADP-ribose polymerase) is involved along with a number of other proteins in single strand break repair (SSBR) and another repair mechanism called base excision repair (BER).

One of the earliest events during single strand DNA repair is the binding of PARP (poly ADP-ribose polymerase) to the break and the rapid synthesis of poly ADP-ribose (PAR) on PARP itself. This molecular structure serves as a signal to recruit other DNA repair proteins, initially XRCC1, which will then repair the break (Mortusewicz, Fouquerel et al. 2011). The signal initiated by these PAR chains is short-lived as they are rapidly degraded by the enzyme PARG. When PARP is bound to PAR, its catalytic activity is reduced and therefore PARG activity helps to restore PARP to its catalytically active form (Curtin and Szabo 2013).

PARG is derived from a single gene with isoforms that reside in the nucleus, mitochondria and cytosol. Another known protein with glycohydrolase activity is ARH3 which is localized to the mitochondria (Mashimo, Kato et al. 2014). Although, known primarily for its direct role in DNA repair, PARG impacts PAR signaling in splicing, transcriptional and epigenetic pathways (Ji and Tulin 2009) (Le May, Iltis et al. 2012) (Dahl, Maturi et al. 2014) (Guastafierro, Catizone et al. 2013) (Caiafa, Guastafierro et al. 2009).

Cancer cells may become reliant upon a specific DNA repair pathway when other mechanisms of DNA repair are non-functional. Tumors carrying mutations in proteins involved in double strand break repair are often more sensitive to PARP inhibitors of SSBR. There is already some evidence that PARG depletion inhibits SSBR and reduces survival of BRCA2-deficient cells (Fathers, Drayton et al. 2012). However, other tumor mutations may give rise to deficiencies in double strand DNA repair mechanisms (so-called "BRCA-ness") thereby sensitizing tumor cells to PARG inhibition.

PARG depletion has been studied in a number of murine and human model systems. Murine cells that are null or depleted for PARG display an increased sensitivity to experimental and clinical DNA damaging agents. However, as deficiency in PARG doesn't sensitize to all agents (e.g. gemcitabine, camptothecin) this suggests a specificity for PARG function with certain pathways of DNA damage repair and chemo- and radiotherapies (Fujihara, Ogino et al. 2009) (Shirai, Fujimori et al. 2013) (Zhou, Feng et al. 2010) (Zhou, Feng et al. 2011).

In humans, PARG depletion sensitizes lung, cervical and pancreatic cancer cells to γ-irradiation or experimental DNA damaging agents (e.g. hydrogen peroxide, Methylmethanesulfonate) (Ame, Fouquerel et al. 2009) (Nakadate, Kodera et al. 2013) (Shirai, Poetsch et al. 2013).

PARP inhibitors are currently undergoing multiple clinical trials where the concept of synthetic lethality or chemosensitization is being explored. Clinical resistance to PARP inhibitors has already been described (Drost and Jonkers 2014) (Barber, Sandhu et al. 2013) and therefore there is a requirement that alternative inhibitors targeting the DNA damage repair machinery are found.

Although current models show that PARG depletion leads to PARP-dependent effects on DNA repair, recent research has shown a mechanistic differentiation from PARP inhibition. Following a genotoxic stimulus depletion of PARG, in contrast to PARP depletion, leads to a drop in NAD levels. This leads to lung cancer cell death as a result of energy failure (Erdelyi, Bai et al. 2009).

Cell permeable PARG inhibitors have been limited to compounds such as Tannic acid or Gallotannin which have questionable specificity for PARG and limited bioavailability (Sun, Zhang et al. 2012) (Fathers, Drayton et al. 2012) (Blenn, Wyrsch et al. 2011).

An object of this invention is to provide cell permeable inhibitors of PARG.

SUMMARY

In one aspect, provided herein is a compound of Formula (I):

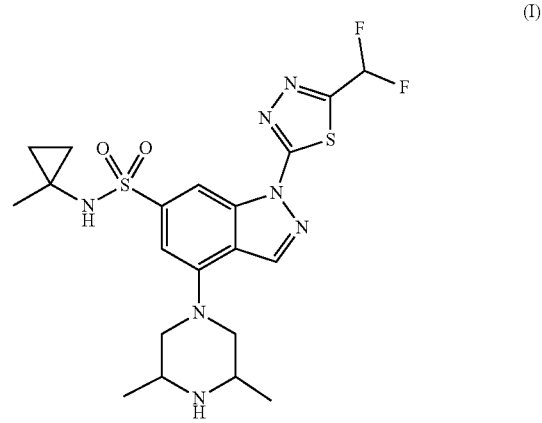 [SMILES: CC1CN(c2cc(S(=O)(=O)NC3(C)CC3)cc3c2cnn3-c2nnc(C(F)F)s2)CC(C)N1]

or a pharmaceutically acceptable salt thereof.

In another aspect, provided herein is a compound of Formula (I)

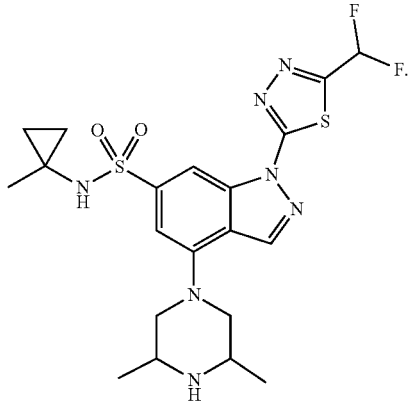

(I)

In another aspect, provided herein is a compound of Formula (A)

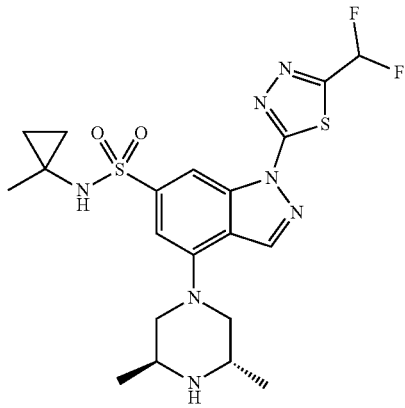

(A)

or a pharmaceutically acceptable salt thereof.

In another aspect, provided herein is a compound of Formula (A)

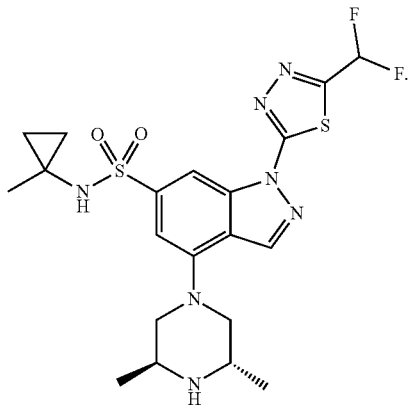

(A)

In another aspect, provided herein is a compound of Formula (B)

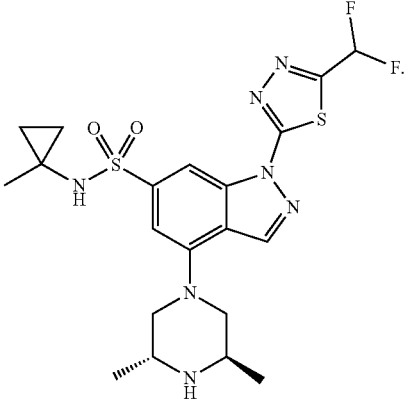

(B)

or a pharmaceutically acceptable salt thereof.

In another aspect, provided herein is a compound of Formula (B)

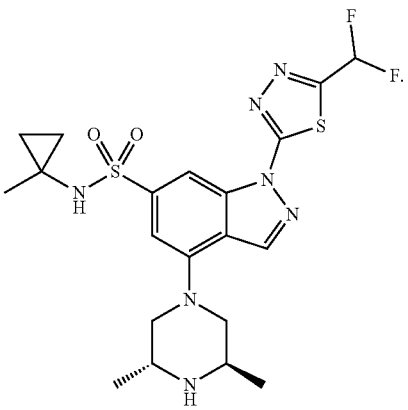

(B)

In another aspect, provided herein is a compound of Formula (C)

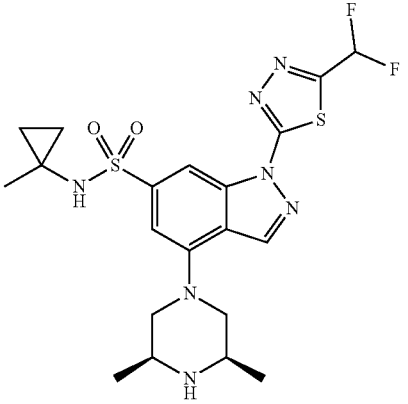

(C)

or a pharmaceutically acceptable salt thereof.

In another aspect, provided herein is a compound of Formula (C)

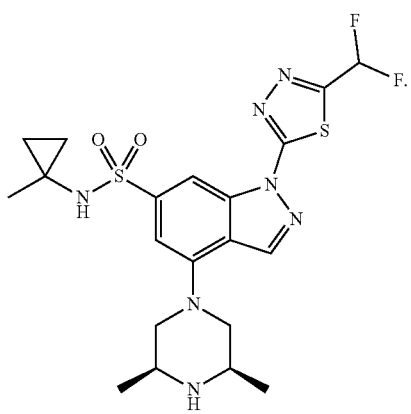

(C)

In another aspect, provided herein is a pharmaceutical composition comprising a compound of Formula (I), Formula (A), Formula (B), or Formula (C), or a pharmaceutically acceptable salt thereof, and one or more pharmaceutically acceptable excipients.

In another aspect, provided herein is a compound of Formula (I), Formula (A), Formula (B), or Formula (C), or a pharmaceutically acceptable salt thereof, or a pharmaceutical composition as defined herein, for use in therapy.

In another aspect, provided herein is a compound of Formula (I), Formula (A), Formula (B), or Formula (C), or a pharmaceutically acceptable salt thereof, or a pharmaceutical composition as defined herein, for use in the treatment of cancer. In one embodiment, the cancer is a human cancer.

In another aspect, provided herein is a compound of Formula (I), Formula (A), Formula (B), or Formula (C), or a pharmaceutically acceptable salt thereof, or a pharmaceutical composition as defined herein, for use in the production of a PARG inhibitory effect.

In another aspect, provided herein is the use of a compound of Formula (I), Formula (A), Formula (B), or Formula (C), or a pharmaceutically acceptable salt thereof, or a pharmaceutical composition as defined herein, in the manufacture of a medicament for use in the treatment of cancer. Suitably, the medicament is for use in the treatment of human cancers.

In another aspect, provided herein is the use of a compound of Formula (I), Formula (A), Formula (B), or Formula (C), or a pharmaceutically acceptable salt thereof, or a pharmaceutical composition as defined herein, in the manufacture of a medicament for use in the production of a PARG inhibitory effect.

In another aspect, provided herein is a method of inhibiting PARG in vitro or in vivo, said method comprising contacting a cell with an effective amount of a compound of Formula (I), Formula (A), Formula (B), or Formula (C), or a pharmaceutically acceptable salt thereof, or a pharmaceutical composition as defined herein.

In another aspect, provided herein is a method of inhibiting cell proliferation in vitro or in vivo, said method comprising contacting a cell with an effective amount of a compound of Formula (I), Formula (A), Formula (B), or Formula (C), or a pharmaceutically acceptable salt thereof, or a pharmaceutical composition as defined herein.

In another aspect, provided herein is a method of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein.

In another aspect, provided herein is a method of treating a cancer resistant to one or more platins or one or more PARP inhibitors in a patient in need thereof, said method comprising administering to said patient an effective amount of a compound Formula (I), Formula (A), Formula (B), or Formula (C), or a pharmaceutically acceptable salt thereof, or a pharmaceutical composition as defined herein.

In another aspect, provided herein is a method of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein, wherein the patient has been previously treated for cancer with a platin.

In another aspect, provided herein is a method of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein, wherein the patient has been previously treated for cancer with a PARP inhibitor.

In another aspect, provided herein is a method of identifying PARG activity in a test compound of PARG inhibitory activity, said method comprising (i) contacting the test compound with isolated PARG enzyme, a biotinylated-PARylated PARP substrate to form a PARG reaction pre-mixture; (ii) contacting the PARG reaction pre-mixture with a detection antibody and streptavidin-europium to form a PARG reaction mixture; and (iii) measuring fluorescence intensity of the PARG reaction mixture, wherein said method further comprises performing steps (i)-(iii) with a positive control sample represented by a compound of Formula (I), Formula (A), Formula (B), or Formula (C), or a pharmaceutically acceptable salt thereof, or a pharmaceutical composition as defined herein. In some embodiments, the detection antibody is an anti-His monoclonal antibody-ULight. In some embodiments the streptavidin-europium binds to the biotinylated-PARylated PARP substrate. In some embodiments fluorescence is measured by providing an excitation wavelength of 317 nM and measuring emissions at 620 nM (streptavidin-europium emission) and 665 nM (ULight emission).

In another aspect, provided are methods of synthesizing a compound of Formula (I), Formula (A), Formula (B), or Formula (C), or a pharmaceutically acceptable salt thereof, as defined herein.

In another aspect, provided herein is a compound of Formula (I), Formula (A), Formula (B), or Formula (C), or a pharmaceutically acceptable salt, obtainable by, or obtained by, or directly obtained by a method of synthesis as defined herein.

In another aspect, provided herein are novel intermediates as defined herein which are suitable for use in any one of the synthetic methods as set out herein.

Preferred, suitable, and optional features of any one particular aspect of the present invention are also preferred, suitable, and optional features of any other aspect.

DETAILED DESCRIPTION OF THE INVENTION

Figure 1:
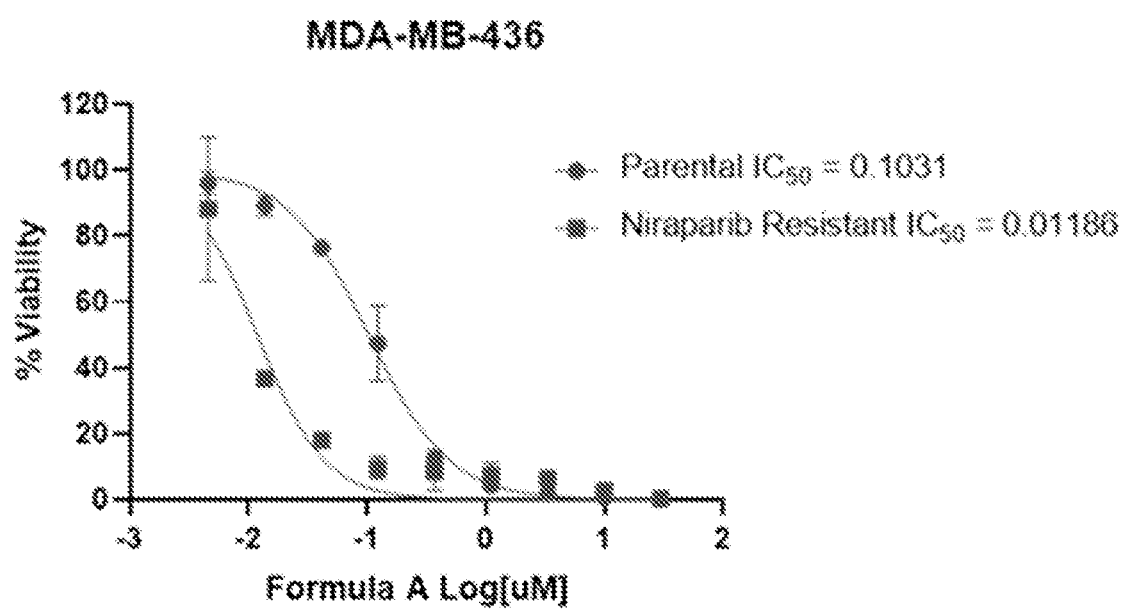
FIG. 1 plots percent viability of PARPi resistant MDA-MB-436 cells as a function of the Log concentration of Formula A as described in Example 4. "Parental IC$_{50}$" refers to the IC$_{50}$ of Formula A before the cells developed PARPi resistance, while "Niraparib resistance IC$_{50}$" refers to the IC$_{50}$ of Formula A after the cells developed PARPi resistance.

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, patient to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

The publications discussed herein are provided solely for their disclosure prior to the filing date of the present application. Further, the dates of publication provided may be different from the actual publication dates, which may need to be independently confirmed.

General

Provided herein are compounds of Formula (I), Formula (A), Formula (B), or Formula (C), or a pharmaceutically acceptable salt thereof, for inhibition of PARG, and pharmaceutical compositions comprising the same. Also provided herein are, for example, methods of treating or preventing a disease, disorder or condition, or a symptom thereof, mediated by inhibition of PARG.

Advantageously, the compounds of the present disclosure are potent inhibitors of PARG in both cellular and in vitro assays. Kinetic solubility studies also demonstrate that these compounds are highly soluble at both pH 2.0 and pH 7.4. Collectively, the combined parameters of the compounds described herein make them ideal compounds for targeting and inhibiting PARG activity.

Definitions

Unless otherwise indicated, the following terms are intended to have the meaning set forth below. Other terms are defined elsewhere throughout the specification.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The term "pharmaceutically acceptable salts" is meant to include salts of a compound of Formula (I), Formula (A), Formula (B), or Formula (C) which are prepared with relatively nontoxic acids or bases, depending on the particular substituents found on the compounds described herein. Base addition salts can be obtained by contacting the neutral form of such compounds with a sufficient amount of the desired base, either neat or in a suitable inert solvent. Examples of salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

Formula (I), Formula (A), Formula (B), or Formula (C) may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of Formula (I), Formula (A), Formula (B), or Formula (C) can have altered pharmacokinetic and pharmacodynamic characteristics which can contribute to enhanced safety, tolerability or efficacy during treatment. All isotopic variations of Formula (I), Formula (A), Formula (B), or Formula (C), whether radioactive or not, are intended to be encompassed within the scope of the present invention.

The terms "patient" or "subject" are used interchangeably to refer to a human or a non-human animal (e.g., a mammal). In one embodiment, the patient or subject is a human.

The terms "administration", "administer" and the like, as they apply to, for example, a patient, cell, tissue, organ, or biological fluid, refer to contact of, for example, an inhibitor of PARG, a pharmaceutical composition comprising same, or a diagnostic agent to the patient, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an inhibitor of PARG or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a patient, or at least one of the symptoms associated with a disease, disorder, condition afflicting a patient. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a patient requires or will benefit from treatment. This judgment is made based on a variety of factors that are in the realm of the physician's or caregiver's expertise.

The terms "prevent", "preventing", "prevention" and the like refer to a course of action (such as administering a PARG inhibitor or a pharmaceutical composition comprising same) initiated in a manner (e.g., prior to the onset of a disease, disorder, condition or symptom thereof) so as to prevent, suppress, inhibit or reduce, either temporarily or permanently, a patient's risk of developing a disease, disorder, condition or the like (as determined by, for example, the absence of clinical symptoms) or delaying the onset thereof, generally in the context of a patient predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a patient requires or will benefit from preventative care. This judgment is made based on a variety of factors that are in the realm of a physician's or caregiver's expertise.

The terms "inhibiting" and "reducing," or any variation of these terms in relation of PARG, includes any measurable decrease or complete inhibition to achieve a desired result. For example, there may be a decrease of about 5%, 10%, 15%, 20%, 25%, 30%, 35%, 40%, 45%, 50%, 55%, 60%, 65%, 70%, 75%, 80%, 85%, 90%, 95%, 99%, or more, reduction of PARG activity compared to normal. About as used herein means within ±10%, preferably ±5% of a given value.

The phrase "therapeutically effective amount" refers to the administration of an agent to a patient, either alone or as part of a pharmaceutical composition and either in a single dose or as part of a series of doses, in an amount capable of having any detectable, positive effect on any symptom, aspect, or characteristic of a disease, disorder or condition when administered to the patient. The therapeutically effective amount can be ascertained by measuring relevant physiological effects, and it can be adjusted in connection with the dosing regimen and diagnostic analysis of the patient's condition, and the like. By way of example, measurement of the serum level of a PARG inhibitor (or, e.g., a metabolite thereof) at a particular time post-administration may be indicative of whether a therapeutically effective amount has been used.

The phrase "platins" or "platinum based-chemotherapeutics" refers to a platinum containing class of chemotherapeutic drug used for treating cancer. Exemplary platins are cisplatin, carboplatin, satraplatin, heptaplatin, picoplatin, nedaplatin, triplatin, lipoplatin, and oxaliplatin.

As used herein, "platin-resistant cancer" or "cancer resistant to one or more platins" refers to cancers that do not respond to treatment with a platin. Nonresponsivness can be assessed by the continued growth of a tumor when administered the agent, a tumor that does not shrink in size when administered the agent, or other known means in the art. Nonresponsivness of a cancer can be determined through clinical observation, diagnosed as such by a medical professional, experimentally tested with isolated cells in a laboratory setting, or by another technical means.

As used herein, "Poly ADP Ribose Polymerase (PARP) inhibitor" refers to an agent that inhibits PARP activity, including PARP1 and PARP2. Examples of PARP inhibitors include, but are not limited to, niraparib, rucaparib, olaparib, talazoparib, and veliparib.

As used herein, "PARP inhibitor-resistant cancer" or "cancer resistant to one or more PARP inhibitors" refers to cancers that do not respond to treatment with a PARP inhibitor. Nonresponsivness can be assessed by the continued growth of a tumor when administered the agent, a tumor that does not shrink in size when administered the agent, or other known means in the art. Nonresponsivness of a cancer can be determined through clinical observation, diagnosed as such by a medical professional, experimentally tested with isolated cells in a laboratory setting, or by another technical means.

As used herein "homologous recombination" refers to the cellular process of genetic recombination in which nucleotide sequences are exchanged between two similar or identical DNA sequences.

As used herein "homologous recombination deficient (HRD) cancer" refers to a cancer that is characterized by a reduction or absence of a functional HR repair pathway. HR deficiency may arise from absence or reduction of one or more HR-associated genes or presence of one or more mutations in one or more HR-associated genes. Examples of HR-associated genes include BRCA1, BRCA2, RAD54, RAD51B, ATM, BARD1, CHECK1, CHECK2, CDK12, RAD51B, RAD54L, RAD51D, PPP22A, BRIP1, CtIP (CtBP-interacting protein), PALB2 (Partner and Localizer of BRCA2), XRCC2 (X-ray repair complementing defective repair in Chinese hamster cells 2), RECQL4 (RecQ Protein-Like 4), BLM (Bloom syndrome, RecQ helicase-like), WRN (Werner syndrome, one or more HR-associated genes) Nbs 1 (Nibrin), and genes encoding Fanconi anemia (FA) proteins or FA-like genes e.g., FANCA, FANCB, FANCC, FANCD1 (BRCA2), FANCD2, FANCE, FANCF, FANCG, FANCI, FANJ (BRIP1), FANCL, FANCM, FANCN (RALB2), FANCP (SLX4), FANCS (BRCA1), RAD51C, and XPF.

Compounds

In one aspect, provided herein is Formula (I)

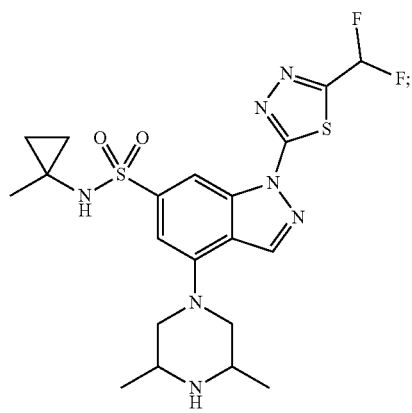

(I)

or a pharmaceutically acceptable salt thereof. In an embodiment, Formula (I) is in a free-base form.

In one aspect, provided herein is Formula (A)

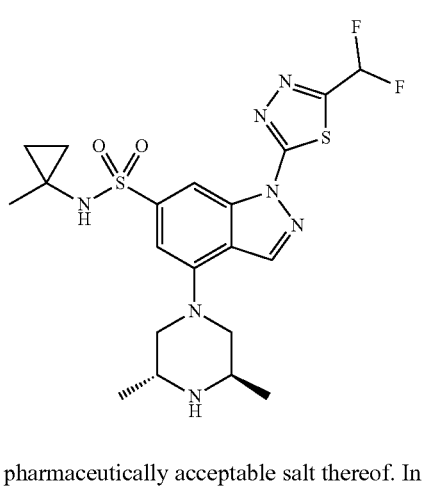

(A)

or a pharmaceutically acceptable salt thereof. In an embodiment, Formula (A) is in a free-base form.

In some embodiments, Formula (A) is at least 70% free of other isomers. In some embodiments, Formula (A) is at least 75% free of other isomers. In some embodiments, Formula (A) is at least 80% free of other isomers. In some embodiments, Formula (A) is at least 85% free of other isomers. In some embodiments, Formula (A) is at least 90% free of other isomers. In some embodiments, Formula (A) is at least 95% free of other isomers. In some embodiments, Formula (A) is at least 99% free of other isomers.

In one aspect, provided herein is Formula (B)

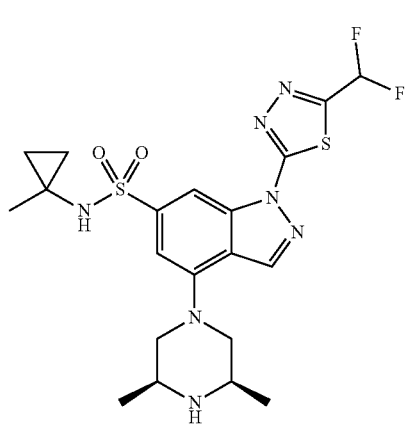

(B)

or a pharmaceutically acceptable salt thereof. In an embodiment, Formula (B) is in a free-base form.

In some embodiments, Formula (B) is at least 70% free of other isomers. In some embodiments, Formula (B) is at least 75% free of other isomers. In some embodiments, Formula (B) is at least 80% free of other isomers. In some embodiments, Formula (B) is at least 85% free of other isomers. In some embodiments, Formula (B) is at least 90% free of other isomers. In some embodiments, Formula (B) is at least 95% free of other isomers. In some embodiments, Formula (B) is at least 99% free of other isomers.

In one aspect, provided herein is Formula (C)

(C)

or a pharmaceutically acceptable salt thereof. In an embodiment, Formula (C) is in a free-base form.

In some embodiments, Formula (C) is at least 70% free of other isomers. In some embodiments, Formula (C) is at least 75% free of other isomers. In some embodiments, Formula (C) is at least 80% free of other isomers. In some embodiments, Formula (C) is at least 85% free of other isomers. In some embodiments, Formula (C) is at least 90% free of other isomers. In some embodiments, Formula (C) is at least 95% free of other isomers. In some embodiments, Formula (C) is at least 99% free of other isomers.

Biological Activity

The PARG enzyme and cell assays described in accompanying Example section may be used to measure the pharmacological effects of the compounds of the present invention.

Pharmaceutical Compositions

Also provided are pharmaceutical compositions which comprise a compound of Formula (I), Formula (A), Formula (B), or Formula (C), or a pharmaceutically acceptable salt thereof, in association with a pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions may be obtained by conventional procedures using conventional pharmaceutical excipients, well known in the art. Thus, compositions intended for oral use may contain, for example, one or more coloring, sweetening, flavoring and/or preservative agents.

An effective amount of a compound of Formula (I), Formula (A), Formula (B), or Formula (C), or a pharmaceutically acceptable salt thereof for use in therapy is an amount sufficient to treat or prevent a proliferative condition referred to herein, slow its progression and/or reduce the symptoms associated with the condition.

The size of the dose for therapeutic or prophylactic purposes of a compound of Formula (I), Formula (A), Formula (B), or Formula (C) will naturally vary according to the nature and severity of the conditions, the age and sex of the animal or patient and the route of administration, according to well-known principles of medicine.

In using a compound of Formula (I), Formula (A), Formula (B), or Formula (C), or a pharmaceutically acceptable salt thereof for therapeutic or prophylactic purposes it will generally be administered so that a total daily dose in the range, for example, 0.01 mg/kg to 100 mg/kg body weight is received. Oral administration may also be suitable, particularly in tablet form.

In some embodiments, compositions of Formula (A) comprise at least 70% of the displayed isomer. In some embodiments, compositions of Formula (A) comprise at least 75% of the displayed isomer. In some embodiments, compositions of Formula (A) comprise at least 80% of the displayed isomer. In some embodiments, compositions of Formula (A) comprise at least 85% of the displayed isomer. In some embodiments, compositions of Formula (A) comprise at least 90% of the displayed isomer. In some embodiments, compositions of Formula (A) comprise at least 95% of the displayed isomer. In some embodiments, compositions of Formula (A) comprise at least 99% of the displayed isomer.

In some embodiments, compositions of Formula (B) comprise at least 70% of the displayed isomer. In some embodiments, compositions of Formula (B) comprise at least 75% of the displayed isomer. In some embodiments, compositions of Formula (B) comprise at least 80% of the displayed isomer. In some embodiments, compositions of Formula (B) comprise at least 85% of the displayed isomer. In some embodiments, compositions of Formula (B) comprise at least 90% of the displayed isomer. In some embodiments, compositions of Formula (B) comprise at least 95% of the displayed isomer. In some embodiments, compositions of Formula (B) comprise at least 99% of the displayed isomer.

In some embodiments, compositions of Formula (C) comprise at least 70% of the displayed isomer. In some embodiments, compositions of Formula (C) comprise at least 75% of the displayed isomer. In some embodiments, compositions of Formula (C) comprise at least 80% of the displayed isomer. In some embodiments, compositions of Formula (C) comprise at least 85% of the displayed isomer. In some embodiments, compositions of Formula (C) comprise at least 90% of the displayed isomer. In some embodiments, compositions of Formula (C) comprise at least 95% of the displayed isomer. In some embodiments, compositions of Formula (C) comprise at least 99% of the displayed isomer.

Therapeutic Uses and Applications

Provided herein are compounds that function as inhibitors of PARG.

The present invention therefore provides a method of inhibiting PARG enzyme activity in vitro or in vivo, said method comprising contacting a cell with an effective amount of a compound of Formula (I), Formula (A), Formula (B), or Formula (C), or a pharmaceutically acceptable salt thereof, or a pharmaceutical composition as defined herein.

The present invention also provides a method of treating a disease or disorder in which PARG activity is implicated in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein. In an embodiment, the disease or disorder is an advanced or metastatic solid tumor. In an embodiment, the disease or disorder is cancer. In an embodiment, the cancer is ovarian, gastric, or breast cancer. In an embodiment, the cancer is lung, cervical, or pancreatic cancer. In an embodiment, the cancer is prostate cancer. In an embodiment, the cancer is a homologous recombinant deficient (HRD) cancer.

Provided herein is a method of inhibiting cell proliferation, in vitro or in vivo, said method comprising contacting a cell with an effective amount of a compound of Formula (I), Formula (A), Formula (B), or Formula (C), or a pharmaceutically acceptable salt thereof, or a pharmaceutical composition as defined herein.

Provided herein is a method of treating a proliferative disorder in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein. In an embodiment, the proliferative disorder is a solid tumor. In an embodiment, the proliferative disorder is a metastatic solid tumor. In an embodiment, the proliferative disorder is cancer. In an embodiment, the cancer is ovarian, gastric, or breast cancer. In an embodiment, the cancer is lung, cervical or pancreatic cancer. In an embodiment, the cancer is prostate cancer. In an embodiment, the cancer is a homologous recombinant deficient (HRD) cancer.

Provided herein is a method of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein. In an embodiment, the cancer is ovarian, gastric, or breast cancer. In an embodiment, the cancer is lung, cervical or pancreatic cancer. In an embodiment, the cancer is a homologous recombinant deficient (HRD) cancer.

Provided herein is a method of treating and/or preventing a homologous recombinant deficient (HRD) cancer in a patient comprising administering to the patient a therapeutically effective amount of a compound of Formula (I), Formula (A), Formula (B), or Formula (C), or a pharmaceutically acceptable salt thereof, or a pharmaceutical composition as defined herein. In an embodiment, the patient is in recognized need of such treatment. In an embodiment, the homologous recombinant deficient (HRD) cancer is breast cancer, ovarian cancer, gastric cancer, prostate cancer, lung cancer, cervical cancer, or pancreatic cancer.

Provided herein is a method of treating and/or preventing a cancer in a patient, where the cancer is characterized by a reduction or absence of BRCA1 and/or BRCA2 gene expression, the absence or mutation of BRCA1 and/or BRCA2 genes, or reduced function of BRCA1 and/or BRCA2 proteins, comprising administering to the patient a therapeutically effective amount of a compound of Formula (I), Formula (A), Formula (B), or Formula (C), or a pharmaceutically acceptable salt thereof, or a pharmaceutical composition as defined herein. In an embodiment, the cancer is ovarian, gastric, or breast cancer. In an embodiment, the cancer is lung, cervical or pancreatic cancer. In an embodiment, the cancer is prostate cancer.

In an embodiment, the cancer is PARP inhibitor-resistant. In some embodiments the PARP inhibitor-resistant cancer is resistant to any one or more of niraparib, olaparib, rucaparib, talazoparib, veliparib, AZD5305, or AZD9574. In some embodiments the PARP inhibitor-resistant cancer is resistant to niraparib. In some embodiments the PARP inhibitor-resistant cancer is resistant to olaparib. In some embodiments, the PARP inhibitor-resistant cancer is ovarian cancer, breast cancer, or pancreatic cancer.

In an embodiment, the cancer is platin-resistant. In some embodiments, the platin-resistant cancer is resistant to any one or more of cisplatin, carboplatin, satraplatin, heptaplatin, picoplatin, nedaplatin, triplatin, lipoplatin, or oxaliplatin. In some embodiments, the platin-resistant cancer is resistant to cisplatin. In some embodiments, the platin-resistant cancer is resistant to carboplatin.

Provided herein are methods of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein, wherein the patient has been determined to be resistant to one or more PARP inhibitors. In some embodiments, said methods comprise administering to said patient a therapeutically effective amount of a compound of Formula (I), Formula (A), Formula (B), or Formula (C), or a pharmaceutically acceptable salt thereof, or a pharmaceutical composition as defined herein, wherein said patient has been diagnosed as resistant to one or more PARP inhibitors.

Provided herein are methods of treating cancer in a patient in need of such treatment, said method comprising administering to said patient a therapeutically effective amount of a compound of Formula (I), Formula (A), Formula (B), or Formula (C), or a pharmaceutically acceptable salt thereof, or a pharmaceutical composition as defined herein, wherein the patient has been determined to be resistant to platinum based chemotherapeutics. In some embodiments, said methods comprise administering to said patient a therapeutically effective amount of a compound of Formula (I), Formula (A), Formula (B), or Formula (C), or a pharmaceutically acceptable salt thereof, or a pharmaceutical composition as defined herein, wherein said patient has been diagnosed as resistant to one or more platinum based chemotherapeutics.

Provided herein is a compound of Formula (I), Formula (A), Formula (B), or Formula (C), or a pharmaceutically acceptable salt thereof, or a pharmaceutical composition as defined herein for use in therapy.

Provided herein is a compound of Formula (I), Formula (A), Formula (B), or Formula (C), or a pharmaceutically acceptable salt thereof, or a pharmaceutical composition as defined herein for use in the treatment of a proliferative condition.

Provided herein is a compound of Formula (I), Formula (A), Formula (B), or Formula (C), or a pharmaceutically acceptable salt thereof, or a pharmaceutical composition as defined herein for use in the treatment of cancer. In a particular embodiment, the cancer is human cancer. In an embodiment, the cancer is ovarian, gastric, or breast cancer. In an embodiment, the cancer is lung, cervical or pancreatic cancer. In an embodiment, the cancer is prostate cancer. In an embodiment, the cancer is a homologous recombinant deficient (HRD) cancer.

Provided herein is a compound of Formula (I), Formula (A), Formula (B), or Formula (C), or a pharmaceutically acceptable salt thereof, or a pharmaceutical composition as defined herein for use in the inhibition of PARG enzyme activity.

Provided herein is a compound of Formula (I), Formula (A), Formula (B), or Formula (C), or a pharmaceutically acceptable salt thereof, or a pharmaceutical composition as defined herein for use in the treatment of a disease or disorder in which PARG activity is implicated.

Provided herein is a use of a compound of Formula (I), Formula (A), Formula (B), or Formula (C), or a pharmaceutically acceptable salt thereof, or a pharmaceutical composition as defined herein in the manufacture of a medicament for the treatment of a proliferative condition.

Provided herein is a use of a compound of Formula (I), Formula (A), Formula (B), or Formula (C), or a pharmaceutically acceptable salt thereof, or a pharmaceutical composition as defined herein in the manufacture of a medicament for the treatment of cancer. Suitably, the medicament is for use in the treatment of human cancers. In an embodiment, the cancer is ovarian, gastric, or breast cancer. In an embodiment, the cancer is lung, cervical or pancreatic cancer. In an embodiment, the cancer is prostate cancer. In an embodiment, the cancer is a homologous recombinant deficient (HRD) cancer.

Provided herein is a use of a compound of Formula (I), Formula (A), Formula (B), or Formula (C), or a pharmaceutically acceptable salt thereof, or a pharmaceutical composition as defined herein in the manufacture of a medicament for the inhibition of PARG enzyme activity.

Provided herein is a use of a compound of Formula (I), Formula (A), Formula (B), or Formula (C), or a pharmaceutically acceptable salt thereof, or a pharmaceutical composition as defined herein in the manufacture of a medicament for the treatment of a disease or disorder in which PARG activity is implicated.

The present disclosure also contemplates the use of the compound of Formula (I), Formula (A), Formula (B), or Formula (C), or a pharmaceutically acceptable salt thereof, or a pharmaceutical composition as defined herein in combination with other therapeutically active agents or compounds as described herein in order to treat the diseases, disorders and conditions contemplated by the present disclosure.

The term "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumors, cancers, leukemias, psoriasis, bone diseases, fibroproliferative disorders (e.g., of connective tissues), and atherosclerosis. Any type of cell may be treated, including but not limited to, lung, colon, breast, ovarian, prostate, gastric, liver, pancreas, brain, and skin. Proliferative disorders also include, for example, advanced or metastatic solid tumors.

The anti-proliferative effects of a compound of Formula (I), Formula (A), Formula (B), or Formula (C), or a pharmaceutically acceptable salt thereof, or a pharmaceutical composition as defined herein have particular application in the treatment of human cancers (by virtue of their inhibition of PARG enzyme activity).

The anti-cancer effect may arise through one or more mechanisms, including but not limited to, the regulation of cell proliferation, the inhibition of angiogenesis (the formation of new blood vessels), the inhibition of metastasis (the spread of a tumor from its origin), the inhibition of invasion (the spread of tumor cells into neighboring normal structures), or the promotion of apoptosis (programmed cell death).

In a particular embodiment of the invention, the proliferative condition to be treated is cancer.

Routes of Administration

A compound of Formula (I), Formula (A), Formula (B), or Formula (C), or a pharmaceutically acceptable salt thereof or pharmaceutical compositions comprising this compound may be administered to a patient by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly. Some embodiments of the present invention contemplate oral administration.

Embodiments

Embodiment 1. A compound of Formula (I):

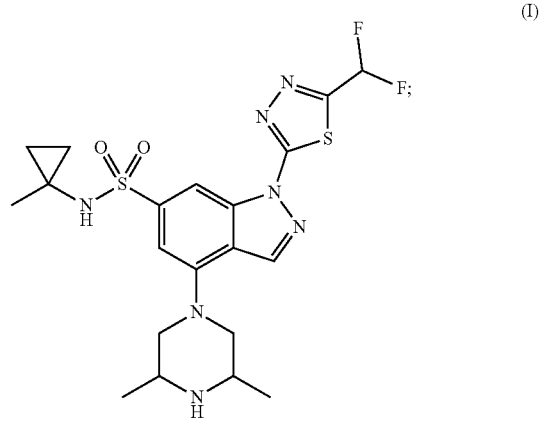 [SMILES: CC1CN(c2cc(S(=O)(=O)NC3(C)CC3)cc3c2cnn3-c2nnc(C(F)F)s2)CC(C)N1]

(I)

or a pharmaceutically acceptable salt thereof.

Embodiment 2. The compound of embodiment 1, represented by Formula (A):

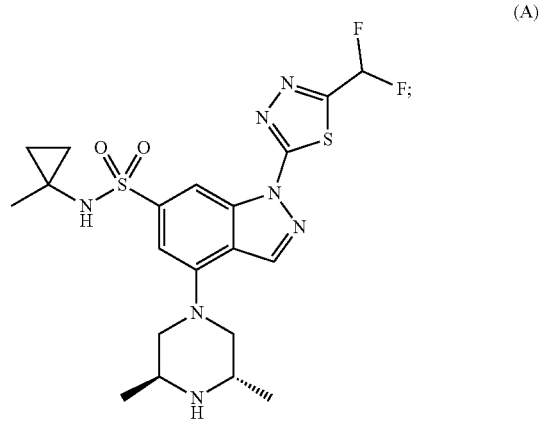 [SMILES: C[C@H]1CN(c2cc(S(=O)(=O)NC3(C)CC3)cc3c2cnn3-c2nnc(C(F)F)s2)C[C@H](C)N1]

(A)

or a pharmaceutically acceptable salt thereof.

Embodiment 3. The compound of embodiment 1 that is in a free-base form.

Embodiment 3A. The compound of embodiment 2, that is in a free-base form.

Embodiment 4. The compound of embodiments 2 or 3A, which is at least 90% free of other isomers.

Embodiment 5. The compound of embodiments 2 or 3A, which is at least 95% free of other isomers.

Embodiment 6. The compound of embodiments 2 or 3A, which is at least 99% free of other isomers.

Embodiment 7. The compound of embodiment 1, represented by Formula (B):

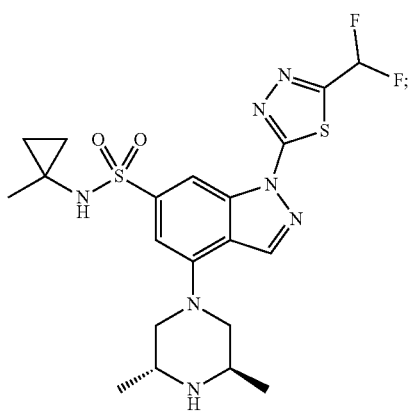

(B)

or a pharmaceutically acceptable salt thereof.

Embodiment 8. The compound of embodiment 7 that is in a free-base form.

Embodiment 9. The compound of embodiments 7 or 8, which is at least 90% free of other isomers.

Embodiment 10. The compound of embodiments 7 or 8, which is at least 95% free of other isomers.

Embodiment 11. The compound of embodiments 7 or 8, which is at least 99% free of other isomers.

Embodiment 12. The compound of embodiment 1, represented by Formula (C):

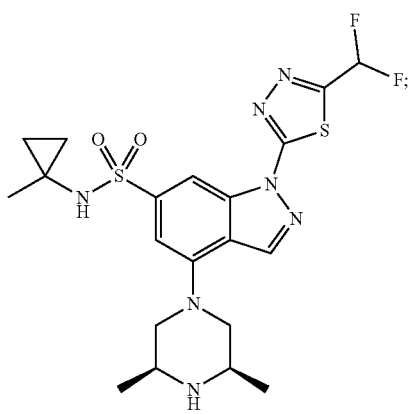

(C)

or a pharmaceutically acceptable salt thereof.

Embodiment 13. The compound of embodiment 12 that is in a free-base form.

Embodiment 14. The compound of embodiments 12 or 13, which is at least 90% free of other isomers.

Embodiment 15. The compound of embodiments 12 or 13, which is at least 95% free of other isomers.

Embodiment 16. The compound of embodiments 12 or 13, which is at least 99% free of other isomers.

Embodiment 17. A pharmaceutical composition comprising a compound or a pharmaceutically acceptable salt thereof of any one of embodiments 1 to 16, and a pharmaceutically acceptable excipient.

Embodiment 18. A method of treating a disease or disorder in which PARG activity is implicated in a patient, said method comprising administering to said patient an effective amount of a compound or a pharmaceutically acceptable salt thereof of any one of embodiments 1 to 16, or a pharmaceutical composition of embodiment 17. Embodiment 18A. The method of embodiment 18, wherein the patient is in recognized need of such treatment and the disease or disorder is cancer. Embodiment 18B. The method of embodiment 18, wherein the disease or disorder is cancer. Embodiment 18B. The method of embodiment 18A or 18B, wherein the cancer is breast cancer, ovarian cancer, gastric cancer, lung cancer, cervical cancer, prostate cancer, or pancreatic cancer.

Embodiment 19. A method of treating a cancer in a patient in need thereof, said method comprising administering to said patient an effective amount of a compound or a pharmaceutically acceptable salt thereof of any one of embodiment 1 to 16, or a pharmaceutical composition of embodiment 17.

Embodiment 20. The method of embodiment 19, wherein said cancer is ovarian, gastric, or breast cancer. Embodiment 20A. The method of embodiment 19, wherein said cancer is lung, cervical or pancreatic cancer. Embodiment 20B. The method of embodiment 19, wherein the cancer is breast cancer, ovarian cancer, gastric cancer, lung cancer, cervical cancer, prostate cancer, or pancreatic cancer.

Embodiment 21. A compound or a pharmaceutically acceptable salt thereof of any one of embodiments 1 to 16, or a pharmaceutical composition of embodiment 17 for use in therapy.

Embodiment 22. The compound or pharmaceutically acceptable salt thereof or the pharmaceutical composition of embodiment 21, wherein said therapy is the treatment of a cancer.

Embodiment 23. The compound or the pharmaceutically acceptable salt thereof or the pharmaceutical composition of embodiment 22, wherein said cancer is ovarian, gastric, or breast cancer. Embodiment 23A. The compound or the pharmaceutically acceptable salt thereof or the pharmaceutical composition of embodiment 22, wherein said cancer is lung, cervical or pancreatic cancer. Embodiment 23B. The compound or the pharmaceutically acceptable salt thereof or the pharmaceutical composition of embodiment 22, wherein the cancer is breast cancer, ovarian cancer, gastric cancer, lung cancer, cervical cancer, prostate cancer, or pancreatic cancer.

Embodiment 24. The use of a compound or a pharmaceutically acceptable salt thereof of any one of embodiments 1 to 16, or a pharmaceutical composition of embodiment 17 in the manufacture of a medicament for use in therapy.

Embodiment 25. The use of embodiment 24, wherein said therapy is the treatment of a cancer.

Embodiment 26. The use of embodiment 25, wherein said cancer is ovarian, gastric, or breast cancer. Embodiment 26A. The use of embodiment 25, wherein said cancer is lung, cervical or pancreatic cancer. Embodiment 26B. The use of embodiment 25, wherein the cancer is breast cancer, ovarian cancer, gastric cancer, lung cancer, cervical cancer, prostate cancer, or pancreatic cancer.

Embodiment 27. A method of inhibiting PARG in vivo, said method comprising administering to a patient an effective amount of a compound or a pharmaceutically acceptable salt thereof of any one of embodiments 1 to 16, or a pharmaceutical composition of embodiment 17. Embodiment 27A. The method of embodiment 27, wherein the patient is in recognized need of such treatment.

Embodiment 28. A method of inhibiting cell proliferation, in vitro or in vivo, said method comprising contacting a cell with an effective amount of a compound or a pharmaceutically acceptable salt thereof of any one of embodiments 1 to 16, or a pharmaceutical composition of embodiment 17. Embodiment 28A. A method of inhibiting cell proliferation, in vitro or in vivo, said method comprising contacting a sample with an effective amount of a compound or a pharmaceutically acceptable salt thereof of any one of embodiments 1 to 16, or a pharmaceutical composition of embodiment 17.

Embodiment 29. A method of treating a cancer resistant to one or more PARP inhibitors in a patient in need thereof, said method comprising administering to said patient an effective amount of a compound or a pharmaceutically acceptable salt thereof of any one of embodiment 1 to 16, or a pharmaceutical composition of embodiment 17. Embodiment 29A. The method of embodiment 29, wherein the patient is in recognized need of such treatment. Embodiment 29B. The method of embodiment 29, wherein the patient has been determined to be resistant to one or more PARP inhibitors. Embodiment 29C. The method of embodiment 29, wherein the patient has been diagnosed as resistant to one or more PARP inhibitors. Embodiment 29D. The method of any one of embodiments 29, 29A, 29B, and 29C, wherein the one or more PARP inhibitors are Talazoparib, Olaparib, Veliparib, Rucaparib, Niraparib, AZD5303, AZD9574, or a pharmaceutically acceptable salt thereof.

Embodiment 30. The method of any one of embodiments 29, 29A, 29B, 29C, and 29D, wherein said cancer is ovarian, gastric, or breast cancer. Embodiment 30A. The method of any one of embodiments 29, 29A, 29B, 29C, and 29D, wherein said cancer is lung, cervical or pancreatic cancer. Embodiment 30B. The method of any one of embodiments 29, 29A, 29B, 29C, and 29D, wherein the cancer is breast cancer, ovarian cancer, gastric cancer, lung cancer, cervical cancer, prostate cancer, or pancreatic cancer.

Embodiment 31. A method of treating a cancer resistant to one or more platins in a patient in need thereof, said method comprising administering to said patient an effective amount of a compound or a pharmaceutically acceptable salt thereof of any one of embodiment 1 to 16, or a pharmaceutical composition of embodiment 17. Embodiment 31A. The method of embodiment 31, wherein the patient is in recognized need of such treatment. Embodiment 31B. The method of embodiment 31, wherein the patient has been determined to be resistant to one or more platins. Embodiment 31C. The method of embodiment 31, wherein the patient has been diagnosed as resistant to one or more platins. Embodiment 31D. The method of any one of embodiments 31, 31A, 31B, and 31C, wherein the one or more platins are cisplatin, carboplatin, satraplatin, heptaplatin, picoplatin, nedaplatin, triplatin, lipoplatin, or oxaliplatin, or a pharmaceutically acceptable salt thereof.

Embodiment 32. The method of embodiment 31, 31A, 31B, 31B, and 31D, wherein said cancer is ovarian, gastric, or breast cancer. Embodiment 32A. The method of embodiment 31, 31A, 31B, 31C, and 31D, wherein said cancer is lung, cervical or pancreatic cancer. Embodiment 32B. The method of any one of embodiments 31, 31A, 31B, 31C, and 31D, wherein the cancer is breast cancer, ovarian cancer, gastric cancer, lung cancer, cervical cancer, prostate cancer, or pancreatic cancer.

Embodiment 33. A method of treating and/or preventing a homologous recombinant deficient (HRD) cancer in a patient comprising administering to the patient a therapeutically effective amount of a compound or a pharmaceutically acceptable salt thereof of any one of embodiment 1 to 16, or a pharmaceutical composition of embodiment 17.

Embodiment 33A. The method of embodiment 33, wherein the patient is in recognized need of such treatment.

Embodiment 34. The method of embodiment 33 or 33A, wherein the HRD cancer is breast cancer, ovarian cancer, gastric cancer, prostate cancer, or pancreatic cancer. Embodiment 34A. The method of embodiment 33 or 33A, wherein the HRD cancer is breast cancer, ovarian cancer, or gastric cancer. Embodiment 34B. The method of embodiment 33 or 33A, wherein the HRD cancer is lung, cervical, or pancreatic cancer.

Embodiment 35. A method of treating and/or preventing a cancer in a patient, where the cancer is characterized by a reduction or absence of BRCA1 and/or BRCA2 gene expression, the absence or mutation of BRCA1 and/or BRCA2 genes, or reduced function of BRCA1 and/or BRCA2 proteins, comprising administering to the patient a therapeutically effective amount of a compound or a pharmaceutically acceptable salt thereof of any one of embodiment 1 to 16, or a pharmaceutical composition of embodiment 17. Embodiment 35A. The method of embodiment 35, wherein the patient is in recognized need of such treatment.

Embodiment 36. The method of embodiment 35 or 35A, wherein the cancer is breast cancer, ovarian cancer, gastric cancer, prostate cancer, or pancreatic cancer. Embodiment 36A. The method of embodiment 35 or 35A, wherein the HRD cancer is breast cancer, ovarian cancer, or gastric cancer. Embodiment 34B. The method of embodiment 35 or 35A, wherein the HRD cancer is lung, cervical, or pancreatic cancer.

Embodiment 37. A PARG inhibitor for use in the treatment of cancer, wherein the PARG inhibitor is a compound of any one of embodiments 1 to 16, or a pharmaceutically acceptable salt thereof, or a pharmaceutical composition of embodiment 17.

Embodiment 38. Use of a PARG inhibitor in the manufacture of a medicament for treating cancer, wherein the PARG inhibitor is a compound of any one of claims 1 to 16, or a pharmaceutically acceptable salt thereof, or a pharmaceutical composition of claim 17.

It is understood that when an embodiment depends from, for example, embodiments 1 to 4, it is dependent on embodiments 1, 2, 3, 3A, and 4. Accordingly, when multiple dependencies are listed, all embodiments within the listed range are included (including embodiments ending in 'A,' 'B,' or any other letter.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

SYNTHESIS EXAMPLES

Example 1: Preparation of Compound of Formula (A)

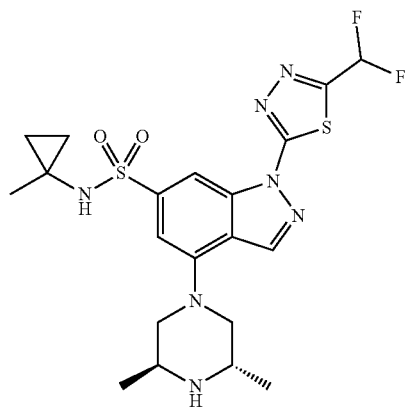

Step 1: Preparation of 2,6-difluoro-4-iodobenzaldehyde

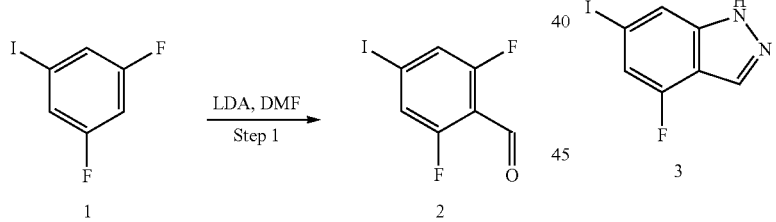

To a stirred solution of 1,3-difluoro-5-iodobenzene (Compound 1) (50 g, 208.3 mmol, Oakwood Chemical, CAS 2265-91-0, catalogue #024566) in THF (500 mL) was added LDA (80 mL, 625.0 mmol) and DMF (48.3 mL, 625 mmol) at −78° C. and stirred at −78° C. for 2 h. After complete consumption of starting material, the reaction mixture was diluted with water (500 mL) and extracted with EtOAc (2×300 mL), the combined organic phases were washed with brine solution (200 mL), dried over anhydrous sodium sulphate, filtered and the filtrate was concentrated under reduced pressure to get crude product as an oil. The crude material was purified by column chromatography using silica gel (100-200) and eluted with 20% EtOAc/Hexane as a gradient. The product was eluted with a gradient of 30% EtOAc/Hexane. The purified fractions were concentrated under reduced pressure to afford 2,6-difluoro-4-iodobenzaldehyde (Compound 2) (23 g) as a solid. $^1$H NMR (500 MHz, CHLOROFORM-d) δ: 10.29 (s, 1H), 7.37-7.46 (m, 2H).

Step 2: Preparation of 4-fluoro-6-iodo-1H-indazole

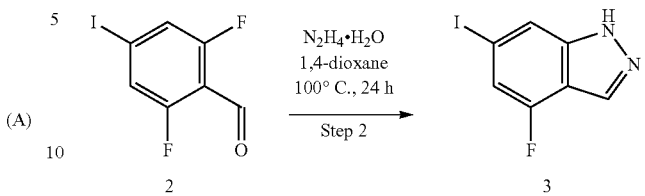

To a stirred solution of 2,6-difluoro-4-iodobenzaldehyde (Compound 2) (5 g, 18.6 mmol) in 1,4 dioxane (110 mL) was added hydrazine hydrate (18.6 mL, 373.1 mmol) at RT and the resulting mixture was stirred at 100° C. for 24 h. The reaction mixture was concentrated under reduced pressure and ice cold water (100 mL) was added. The mixture was stirred for 30 min during which time solid was precipitated out. The mixture was filtered. The solid was washed with water (100 mL), n-pentane (50 mL), and dried under vacuum to afford product 4-fluoro-6-iodo-1H-indazole (Compound 3) (2.3 g) as a solid. MS ESI calculated for $C_7H_4FIN_2$ [M+H]$^+$ 262.94, found 262.99. $^1$H NMR (CDCl$_3$, 400 MHz): 10.12 (s, 1H), 8.10 (s, 1H), 7.70 (s, 1H), 7.15 (dd, J=9 Hz, 1H).

Step 3: Preparation of 2-(difluoromethyl)-5-(4-fluoro-6-iodo-1H-indazol-1-yl)-1,3,4-thiadiazole

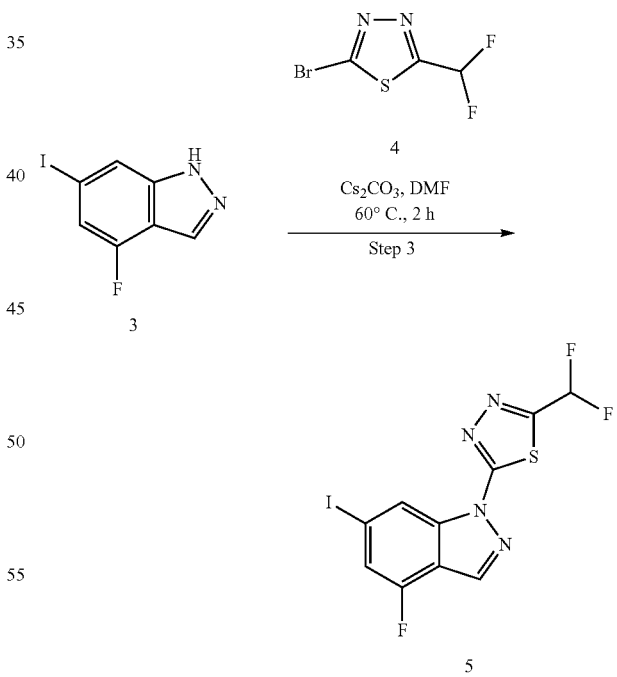

To a stirred solution of 4-fluoro-6-iodo-1H-indazole (Compound 3) (5 g, 19.0 mmol) in DMF (50 mL) was added cesium carbonate (18.6 g, 57.24 mmol) and 2-bromo-5-(difluoromethyl)-1,3,4-thiadiazole (Compound 4) (3.8 g, 18.1 mmol, Enamine Stock Building Blocks, CAS 1340313-49-6, catalogue #EN300-108825). The resulting mixture was stirred at 60° C. for 2 h. The progress of the reaction was monitored by TLC. The reaction mixture was quenched with ice cold water (50 mL) and stirred for 30 min during which time solid precipitated out. The mixture was filtered. The solid collected was washed with water (100 mL) followed by n-pentane (100 mL), and dried under vacuum to afford 2-(difluoromethyl)-5-(4-fluoro-6-iodo-1H-indazol-1-yl)-1,3,4-thiadiazole (Compound 5) (4.2 g) as a solid. MS ESI calculated for $C_{10}H_4F_3IN_4S$ [M+H]$^+$ 396.92, found 396.91. $^1$H NMR (CDCl$_3$, 500 MHz): 8.87 (s, 1H), 8.29 (s, 1H), 7.40 (dd, J=17 Hz, 1H), 7.0 (t, J=53.5 Hz, 1H).

Step 4: Preparation of S-(1-(5-(difluoromethyl)-1,3,4-thiadiazol-2-yl)-4-fluoro-1H-indazol-6-yl) benzothioate

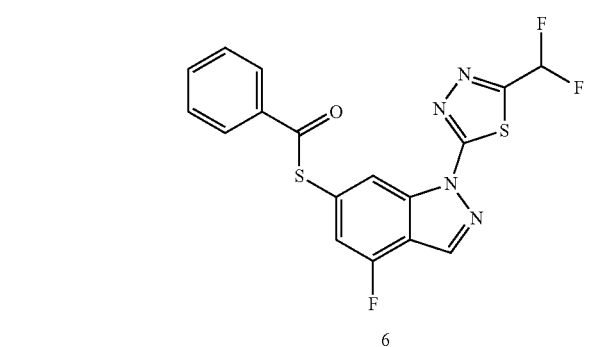

Step 5: Preparation of N-(1-cyanocyclopropyl)-1-(5-(difluoromethyl)-1,3,4-thiadiazol-2-yl)-4-fluoro-1H-indazole-6-sulfonamide

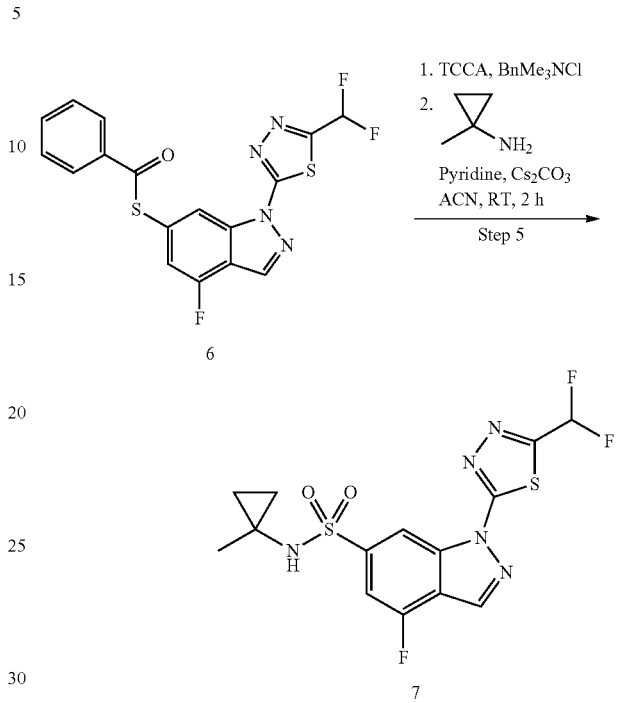

To a stirred solution of 2-(difluoromethyl)-5-(4-fluoro-6-iodo-1H-indazol-1-yl)-1,3,4-thiadiazole (Compound 5) (100 mg, 0.25 mmol) in toluene (1 mL) degassed for 5 min, was added CuI (5 mg, 0.025 mmol), 1,10-phenanthroline (phen) (11 mg, 0.05 mmol), and potassium thiobenzoate (67 mg, 0.378 mmol) at RT. The resulting mixture was stirred at 100° C. for 16 h. The progress of the reaction was monitored by LCMS. The crude mixture was purified by column chromatography using silica gel (100-200) and eluted with 10% EtOAc/Hexane as a gradient. The purified fractions were collected and concentrated under reduced pressure to afford S-(1-(5-(difluoromethyl)-1,3,4-thiadiazol-2-yl)-4-fluoro-1H-indazol-6-yl) benzothioate (Compound 6) (55 mg) as a solid. MS ESI calculated for $C_{17}H_9F_3N_4OS_2$ [M+H]$^+$ 407.02, found 407.01. $^1$H NMR (CDCl$_3$, 400 MHz): 8.68 (s, 1H), 8.39 (s, 1H), 8.03 (d, J=7.6 Hz, 2H), 7.64 (t, J=7.2 Hz, 1H), 7.53 (t, J=7.6 Hz, 2H), 7.27 (s, 1H), 6.99 (t, J=53.2 Hz, 1H).

To a stirred solution of S-(1-(5-(difluoromethyl)-1,3,4-thiadiazol-2-yl)-4-fluoro-1H-indazol-6-yl) benzothioate (Compound 6) (500 mg, 1.23 mmol) in acetonitrile (10 mL) at 0° C. were added a solution of BnMe$_3$NCl (682 mg, 3.69 mmol), and TCCA (trichloroisocyanuricacid) (370 mg 1.59 mmol) in acetonitrile (40 mL). The reaction mixture was stirred for 20 min. Then a solution of 1-methyl cyclopropane-1-amine (1.71 g, 7.38 mmol, Combi-Blocks, CAS 22936-83-0, catalogue #QH-3639) in pyridine (2.5 mL) and cesium carbonate (198 mg, 0.61 mmol) were added to the reaction mixture at 0° C. and stirred at RT for 2 h. The progress of the reaction was monitored by LCMS. LCMS showed complete consumption of starting material (S-(1-(5-(difluoromethyl)-1,3,4-thiadiazol-2-yl)-4-fluoro-1H-indazol-6-yl) benzothioate) (Compound 6). The reaction mixture was diluted with water (50 mL) and extracted with EtOAc (2×30 mL). The combined organic layer was washed with brine solution (20 mL), dried over anhydrous sodium sulphate, filtered and the filtrate was concentrated under reduced pressure to obtain crude product. The crude product was purified by column chromatography using silica gel (100-200) and eluted with 5 to 50% EtOAc/hexane as a gradient. The product was eluted at 20% EtOAc/hexane. The purified fractions were collected and concentrated under reduced pressure to afford 1-(5-(difluoromethyl)-1,3,4-thiadiazol-2-yl)-4-fluoro-N-(1-methylcyclopropyl)-1H-indazole-6-sulfonamide (Compound 7) (90 mg) as a solid. MS ESI calculated for $C_{14}H_9F_3N_6O_2S_2$[M+H]$^+$ 404.04, found 404.18. $^1$H NMR (CDCl$_3$, 400 MHz): 9.00 (s, 1H), 8.80 (s, 1H), 8.54 (s, 1H), 7.63 (t, J=48.8 Hz, 2H), 1.10 (s, 3H), 0.65 (s, 2H), 0.44 (s, 2H).

Step 6: Preparation of tert-butyl (2S,6S)-4-(1-(5-(difluoromethyl)-1,3,4-thiadiazol-2-yl)-6-(N-(1-methylcyclopropyl)sulfamoyl)-1H-indazol-4-yl)-2,6-dimethylpiperazine-1-carboxylate Step 7: Preparation of 1-(5-(difluoromethyl)-1,3,4-thiadiazol-2-yl)-4-((3S,5S)-3,5-dimethylpiperazin-1-yl)-N-(1-methylcyclopropyl)-1H-indazole-6-sulfonamide (Formula A)

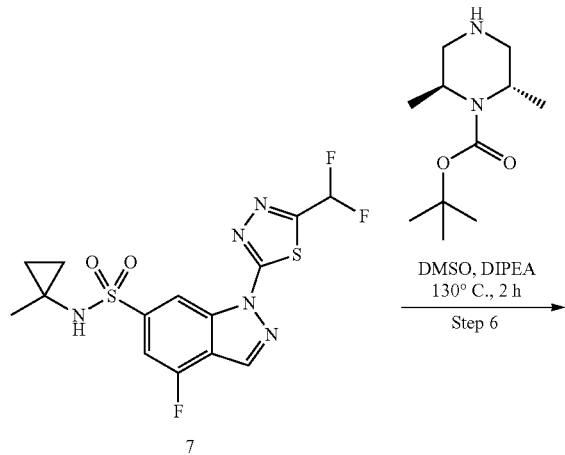

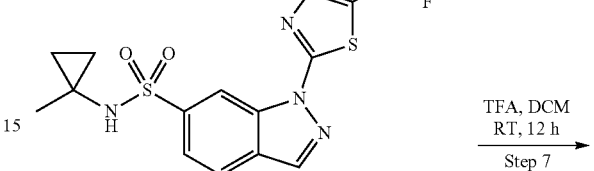

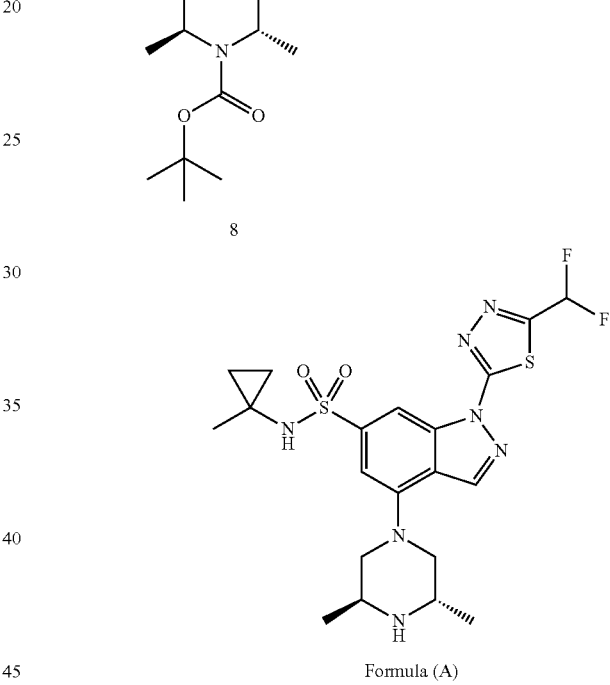

To a stirred solution of 1-(5-(difluoromethyl)-1,3,4-thiadiazol-2-yl)-4-fluoro-N-(1-methylcyclopropyl)-1H-indazole-6-sulfonamide (Compound 7) (80 mg, 0.19 mmol) in DMSO (dimethyl sulfoxide) (2 mL) were added tert-butyl (2S,6S)-2,6-dimethylpiperazine-1-carboxylate (85 mg, 0.39 mmol, BLD Pharmatech, CAS 574007-66-2, catalogue #BD233798) and DIPEA (N,N-diisopropyl ethylamine) (0.1 mL, 0.59 mmol) and reaction mixture was stirred at 130° C. for 2 h. The reaction mixture was quenched with ice cold water (20 mL) and stirred for 30 min. The obtained solid was filtered, washed with water (10 mL), dried under vacuum and purified by column chromatography over silica gel (100-200) and eluted with 50% EtOAc/hexane as a gradient, purified fractions concentrated under reduced pressure to afford tert-butyl (2S,6S)-4-(1-(5-(difluoromethyl)-1,3,4-thiadiazol-2-yl)-6-(N-(1-methylcyclopropyl) sulfamoyl)-1H-indazol-4-yl)-2,6-dimethylpiperazine-1-carboxylate (Compound 8) (110 mg, yield: 92%) as a solid. MS ESI calculated for $C_{25}H_{33}F_2N_7O_4S_2$ [M+H]$^+$ 598.20, found 598.26.

To a stirred solution of tert-butyl (2S,6S)-4-(1-(5-(difluoromethyl)-1,3,4-thiadiazol-2-yl)-6-(N-(1-methylcyclopropyl)sulfamoyl)-1H-indazol-4-yl)-2,6-dimethyl piperazine-1-carboxylate (Compound 8) (100 mg, 0.16 mmol) in DCM (3 mL) was added trifluoroacetic acid (0.07 mL, 0.98 mmol) at 0° C. and reaction mixture was stirred at RT for 12 h. The reaction mixture was concentrated under reduced pressure, purified by Prep HPLC purification (Prep HPLC conditions: MOBILE PHASE—10 mM ammonium bicarbonate in H$_2$O: MeCN COLUMN—Inertsil ODS (20×250) mm 5u Flow-18 ml/min GRADIENT METHOD-0/50, 9.5/82, 9.55/99, 11.5/99, 11.55/50, 14.5/50, SOLUBILITY: CAN, Fraction Volume: 100 mL) to afford 1-(5-(difluoromethyl)-1,3,4-thiadiazol-2-yl)-4-((3S,5S)-3,5-dimethylpiperazin-1-yl)-N-(1-methylcyclopropyl)-1H-indazole-6-sulfonamide (Formula A) (18 mg, yield: 21%) as a solid. MS ESI calculated for $C_{20}H_{25}F_2N_7O_2S_2$ [M+H]$^+$ 498.15, found 498.34. $^1$H NMR (DMSO-d$_6$, 400 MHz): δ (ppm) 8.75 (s, 1H), 8.40 (s, 1H), 8.31 (s, 1H), 7.59 (t, J=52.8 Hz, 1H), 7.10 (d, J=1.0 Hz, 1H), 3.37 (br dd, J=11.5, 2.9 Hz, 2H), 3.22-3.30 (m, 2H), 3.08 (br dd, J=11.7, 6.1 Hz, 2H), 1.17 (d, J=6.4 Hz, 6H), 1.08 (s, 3H), 0.58-0.76 (m, 2H), 0.29-0.49 (m, 2H).

Example 2: Preparation of Compound of Formula (B)

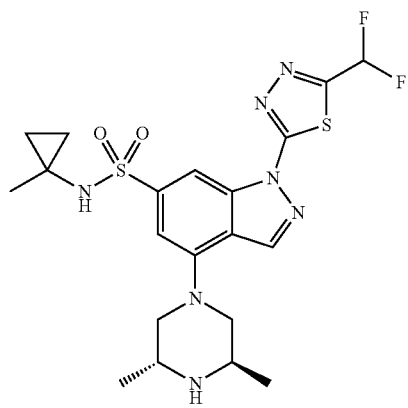

(B)

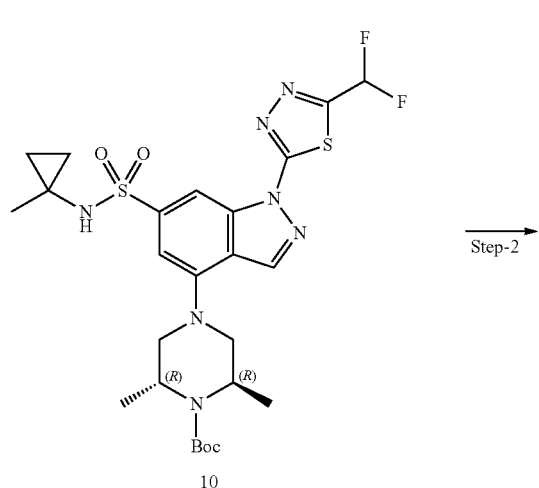

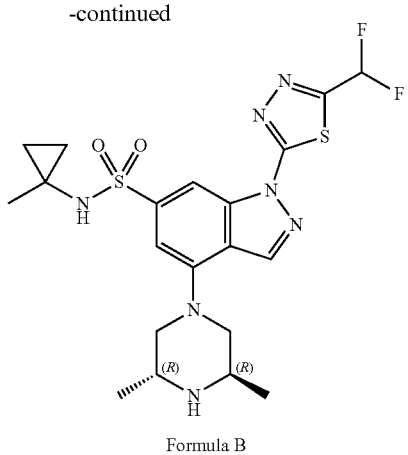

Formula B

Step 1: Preparation of tert-butyl (2R,6R)-4-(1-(5-(difluoromethyl)-1,3,4-thiadiazol-2-yl)-6-(N-(1-methylcyclopropyl)sulfamoyl)-1H-indazol-4-yl)-2,6-dimethylpiperazine-1-carboxylate To a stirred solution of 1-(5-(difluoromethyl)-1,3,4-thiadiazol-2-yl)-4-fluoro-N-(1-methylcyclopropyl)-1H-indazole-6-sulfonamide (Compound 7) (0.25 g, 0.62 mmol) in DMSO (2 mL) was added DIPEA (0.31 mL, 1.859 mmol) and tert-butyl (2R,6R)-2,6-dimethylpiperazine-1-carboxylate (Compound 9) (0.266 g, 1.239 mmol) (Pharmablock, CAS 574007-62-8, Part No: PB05909) at room temperature. The reaction mixture was stirred at 110° C. for 16 h. The reaction mixture was quenched with water (50 mL) and extracted with EtOAc (2×50 mL). Combined organic layers were dried over sodium sulphate, filtered and concentrated under reduced pressure. The crude compound was purified by flash chromatography (conditions: MOBIL PHASE (A): Hexane MOBIL PHASE (B): EtOAc COLUMN: Silica gel (40 g) METHOD: Gradient). Pure fractions concentrated under reduced pressure to afford tert-butyl (2R,6R)-4-(1-(5-(difluoromethyl)-1,3,4-thiadiazol-2-yl)-6-(N-(1-methylcyclopropyl)sulfamoyl)-1H-indazol-4-yl)-2,6-dimethylpiperazine-1-carboxylate (Compound 10) (0.21 g, yield: 57%) as an off white solid. MS ESI calculated for $C_{25}H_{33}F_2N_7O_4S_2$ [M−H]$^+$ 596.20, found 596.62.

Step 2: Preparation of 1-(5-(difluoromethyl)-1,3,4-thiadiazol-2-yl)-4-((3R,5R)-3,5-dimethylpiperazin-1-yl)-N-(1-methylcyclopropyl)-1H-indazole-6-sulfonamide (Formula B)

To a stirred solution of tert-butyl (2R,6R)-4-(1-(5-(difluoromethyl)-1,3,4-thiadiazol-2-yl)-6-(N-(1-methylcyclopropyl)sulfamoyl)-1H-indazol-4-yl)-2,6-dimethylpiperazine-1-carboxylate (Compound 10) (0.2 g, 0.335 mmol) in DCM (5 mL) was added Trifluoroacetic acid (0.1 mL, 1.338 mmol) at 0° C. The reaction mixture was stirred at room temperature for 3 h. The reaction mixture was quenched with saturated sodium bicarbonate solution (50 mL) and extracted with EtOAc (2×50 mL). Combined organic layer was dried over sodium sulphate, filtered and concentrated under reduced pressure to afford 1-(5-(difluoromethyl)-1,3,4-thiadiazol-2-yl)-4-((3R,5R)-3,5-dimethylpiperazin-1-yl)-N-(1-methylcyclopropyl)-1H-indazole-6-sulfonamide (Formula B) (130 mg, yield: 89.2%) as a pale yellow solid. MS ESI calculated for $C_{20}H_{25}F_2N_7O_2S_2$ [M+H]$^+$ 498.15, found 498.30. $^1$H NMR (400 MHz, DMSO-d$_6$): δ (ppm) 8.75 (s, 1H), 8.40 (s, 1H), 8.31 (s, 1H), 7.60 (t, J=53.0 Hz, 1H), 7.11 (s, 1H), 3.30-3.42 (m, 4H), 3.05-3.15 (m, 2H), 1.15-1.28 (m, 7H), 1.07 (s, 3H), 0.60-0.70 (m, 2H), 0.38 (s, 2H).

Example 3: Preparation of Compound of Formula (C)

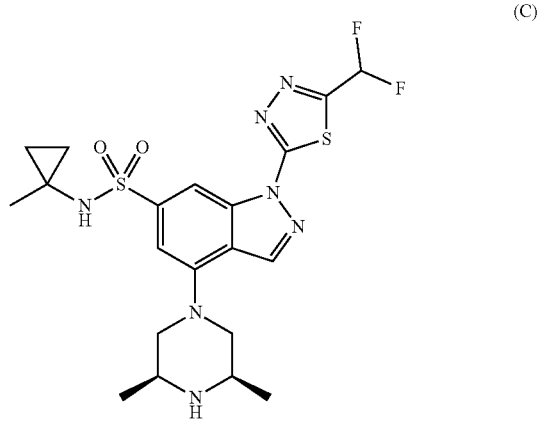 [SMILES: C[C@@H]1CN(c2cc(S(=O)(=O)NC3(C)CC3)cc3c2cnn3-c2nnc(C(F)F)s2)C[C@H](C)N1]

Preparation of 1-(5-(difluoromethyl)-1,3,4-thiadiazol-2-yl)-4-((3S,5R)-3,5-dimethylpiperazin-1-yl)-N-(1-methylcyclopropyl)-1H-indazole-6-sulfonamide (Formula C)

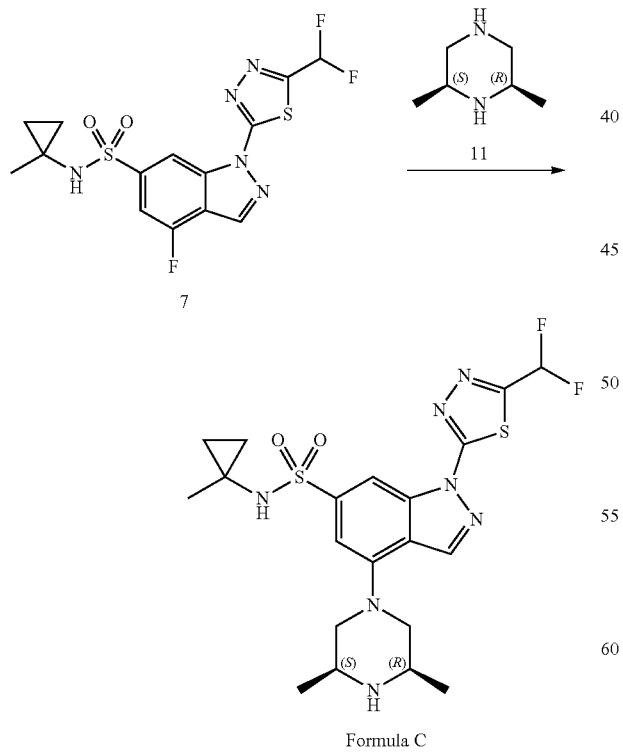

Formula C

A solution of 1-(5-(difluoromethyl)-1,3,4-thiadiazol-2-yl)-4-fluoro-N-(1-methylcyclopropyl)-1H-indazole-6-sulfonamide (Compound 7) (12.0 g, 29.7 mmol) and cis-2,6-dimethylpiperazine (Compound 11) (8.49 g, 74.4 mmol) (Combi-Blocks, CAS 21655-48-1, catalogue #OR-0130) in NMP (120 mL) was stirred for 18 h at 50° C. under N$_2$ protection. The reaction mixture was cooled to RT (25° C.) and combined with another batch of reaction mixture where 1.0 g of Compound 7 was used. Water (260 mL) was slowly added to the combined reaction mixtures below 25° C. and stirred for 2 h. The reaction mixture was filtered and the solid was washed with water (26 mL) to afford 1-(5-(difluoromethyl)-1,3,4-thiadiazol-2-yl)-4-((3S,5R)-3,5-dimethylpiperazin-1-yl)-N-(1-methylcyclopropyl)-1H-indazole-6-sulfonamide (Formula C) (15.6 g) as light yellow solid. MS ESI calculated for C$_{20}$H$_{25}$F$_2$N$_7$O$_2$S$_2$ [M+H]$^+$ 498.15, found 498.04, $^1$H NMR (DMSO-d$_6$, 400 MHz): δ (ppm) 8.89 (d, J=0.7 Hz, 1H), 8.42 (s, 1H), 8.31 (s, 1H), 7.59 (t, J=53.2 Hz, 1H), 7.12 (d, J=1.2 Hz, 1H), 3.66 (br d, J=10.0 Hz, 2H), 2.94-3.11 (m, 2H), 2.43-2.49 (m, 2H), 2.23-2.30 (m, 1H), 1.07 (d, J=5.4 Hz, 9H), 0.61-0.71 (m, 2H), 0.35-0.44 (m, 2H).

BIOLOGICAL EXAMPLES

Example 1

Inhibition of PARG Enzymatic Assay (TR-FRET)

Enzymatic EC$_{50}$ Assay

PARG enzyme was incubated with compound or vehicle (DMSO) and the biotinylated-PARylated PARP-1 substrate in a microtiter plate. After adding detection antibody and streptavidin-europium, and then incubating, the plate was read for fluorescence intensity. The low control (DMSO) with low fluorescence intensity represents no inhibition of enzymatic activity, while the high control (no enzyme) with high fluorescence intensity represents full inhibition of enzymatic activity.

Materials

Enzyme:
　PARG
　　hPARG: 250 pM, 1-976, His-tagged, Proteos, 2.0 mg/mL (17.9 μM)
　Substrate: 30 nM
　Test Compound/Enzyme Pre-incubation time: 1 hr
　Enzyme/Substrate Reaction time: 10 minutes
　Substrate: hPARP1, His6-TEV tagged, 1.2 mg/mL (10.3 μM)
　Detection Antibody: anti-His monoclonal antibody-ULight, Perkin Elmer catalog #TRF0134-M
　Streptavidin-Europium: Perkin Elmer catalog #AD0062
　Assay Buffer: 50 mM Tris-HCL pH 7.4, 50 mM KCL, 3 mM EDTA, 0.4 mM EGTA, 1 mM DTT, 0.01% Tween 20, 0.01% BSA
　Temperature: 23° C.
　Total reaction volume: 20 μL
Controls:
　0% inhibition: DMSO
　100% inhibition: No enzyme
Enzyme reaction and Detection:
　1. Transfer 200 nL of 100× compound or DMSO to the appropriate wells of a 384 well white polystyrene microtitre plate (Corning Catalog #3574).
　2. Transfer 10 uL of 2× final concentration of enzyme in assay buffer or assay buffer alone to the appropriate wells.

3. Centrifuge the plate at 1000 rpm for 30 seconds.
4. Incubate the plate at room temperature for 1 hour.
5. Transfer 10 uL of 2× substrate in assay buffer to all test wells.
6. Incubate the plate at room temperature for 10 minutes
7. Transfer 10 uL of 3× mixture of 42 nM detection antibody and 2.25 nM streptavidin-europium in 50 mM Tris-HCL pH 7.4 to all test wells.
8. Incubate the plate at room temperature for 1 hour.
9. Read the plate on a plate reader (Envision)
   Excitation: 317 nM
   Emission: 620 nM
   Emission: 665 nM Data Analysis:

$EC_{50}$ values were calculated in Collaborative Drug Discovery vault (CDD). Curves were fitted by CDD as response (%) vs compound concentration (uM) using a 4-parameter inhibition model using Formula 1.

$$\text{Fit} = (A + ((B-A)/(1+((C/x)^D))))$$

$$\text{Res} = (y-\text{fit}) \qquad \text{Formula 1:}$$

The TR-FRET $EC_{50}$ values for Formula (A), Formula (B), Formula (C), and select comparators are provided in Table 1, below.

Example 2

Cellular Viability Assay

The ability of the compounds disclosed herein to inhibit PARG was determined in the following two cell lines: RMUGS-NucLight Red and SNU601-NucLight Red. RMUGS-NucLight Red and SNU601-NucLight Red cells were generated by stably transducing parental cells (RMUGS-JCRB Cell Bank, Cat no: IF050320; SNU601-Korean Cell Line Bank, Cat no: 00601) with Incucyte® NucLight Red lentivirus (Sartorius, Cat no: 4476). Described below are the protocols followed for both the cell lines.

SNU601-NucLight Red:

The cells were plated at 200 cells/well in a 384-well black plate with clear flat bottom. After 24 hours, the plates were imaged using the Incucyte® S3 Live-Cell Analysis system and the number of live cells in each well (Day 0) was counted. Test compounds were then added by Tecan digital dispenser to generate a 9 point dose curve with a 3 fold dilution and 10 uM top concentration. All treatments were done in triplicates. After 7 days of incubation, the plates were imaged using the Incucyte® S3 system and the number of live cells per well (Day 7) was counted. For every well on the plate, the live cell counts on day 7 was normalized to the cell counts from day 0 (Day 7/Day 0). Average values of DMSO treated wells in a plate were calculated. All the data points were normalized to that of the average DMSO value. The % of control for each sample was compared to DMSO treated control samples. $EC_{50}$ values were calculated in Collaborative Drug Discovery vault (CDD). Curves were fitted by CDD as % of control vs. log [compound concentration] using a 4-parameter inhibition model (Levenberg-Marquardt algorithm):

$$\text{Fit} = (A + ((B-A)/(1+((C/x)^D))))$$

$$\text{Res} = (y-\text{fit})$$

When clear bi-phasic behavior was observed on the resulting data the $EC_{50}$ was calculated in GraphPad Prism Software for the major fraction of the response using the following formula:

Span=Top-Bottom

Section1=Span*Frac/(1+10^((Log $EC_{50\_1}$–X)*nH1))

Section2=Span*(1–Frac)/(1+10^((Log $EC_{50\_2}$–X)*nH2))

Y=Bottom+Section1+Section2

Frac=fraction of the more potent response between the top (100) and bottom (0) of the normalized curve $EC_{50\_1}$, $EC_{50\_2}$=$EC_{50}$ of the respective response curves 1 and 2 in each fraction nH1, nH2=normalized Hill Slopes of the respective response curves 1 and 2 in each fraction X=log (concentration)

RMUGS-NucLight Red:

The cells were plated at 1000 cells/well in a 96-well black plate with clear flat bottom. After 24 hours, the plates were imaged using the Incucyte® S3 Live-Cell Analysis system and the number of live cells in each well (Day 0) was counted. Test compounds were then added by Tecan digital dispenser to generate a 9 point dose curve with a 3 fold dilution and 10 uM top concentration. All treatments were done in duplicates. After 7 days of incubation, the plates were imaged using the Incucyte® S3 system and the number of live cells per well (Day 7) was counted. For every well on the plate, the live cell counts on day 7 was normalized to the cell counts from day 0 (Day 7/Day 0). Average values of DMSO treated wells in a plate were calculated. All the data points were normalized to that of the average DMSO value. The % of control for each sample was compared to DMSO treated control samples. $EC_5$ values were calculated in Collaborative Drug Discovery vault (CDD). Curves were fitted by CDD as % of control vs. log [compound concentration] using a 4-parameter inhibition model (Levenberg-Marquardt algorithm):

$$\text{Fit} = (A + ((B-A)/(1+((C/x)^D))))$$

$$\text{Res} = (y-\text{fit})$$

The SNU601-NucLight Red and RMUGS-NucLight Red results for Formula (A), Formula (B), Formula (C), and select comparators are provided in Table 1, below.

Example 3

Kinetic Solubility Determinations in PBS pH 2.0 and pH 7.4

Kinetic Solubility Assay

Materials

Enzyme:
   Control compound diclofenac sodium (LOT #BCBW9128) was purchased from Sigma Chemical Co.
   1.5 mL glass flat bottom vials (BioTech Solutions)
   Molded PTFE/SIL plugs (BioTech Solutions)
   PTFE encapsulated stir stick (V&P Scientific)
   MultiScreenHTS HV (0.45 μm) 96 well plate (Millipore, MSHVN4510 or MSHVN4550)
   Eppendorf Thermomixer Comfort
   Vacuum Manifold ORVMN96.

PBS pH 2.0 and pH 7.4 was prepared in our laboratory

Controls:
  diclofenac sodium (LOT #BCBW9128), Sigma Chemical Co.

Kinetic Solubility Protocol:
1. Preparation of stock solutions. The stock solutions of test compounds and control compound diclofenac sodium were prepared in DMSO at the concentration of 30 mM and 10 mM, respectively.
2. Procedure for solubility determination. 10 µL of stock solutions (30 mM) of test compounds was placed in order into their proper 96-well rack, 20 µL of DMSO and 970 µL of PBS pH 2.0 or pH 7.4 was added into each vial of the cap-less Solubility Sample plate; 30 µL of stock solution (10 mM) of control compound was placed in order into its proper 96-well rack, 970 µL of PBS pH 2.0 or pH 7.4 was added into each vial of the cap-less Solubility Sample plate. The assay was performed in duplicate. One stir stick was added to each vial and seal using a molded PTFE/Silicone plug. Then the Solubility Sample plate was transferred to the Eppendorf Thermomixer Comfort plate shaker and shaken at 25° C. at 1100 RPM for 24 hours. After completion of the 24 hours, plugs were removed and the stir sticks were removed using a big magnet, the samples from the Solubility Sample plate were transferred into the filter plate. Using the Vacuum Manifold, all the samples were filtered. Aliquot of 10 µL was taken from the filtrate followed by addition of 990 µL of a mixture of H2O and acetonitrile (1:1 in v/v). 200 µL of diluent was transferred to a new 96-well plate for LC-MS/MS analysis. The dilution factor was changed according to the solubility values and the LC-MS signal response.
3. Preparation of 3 µM standards (STD). From the 10 mM or 30 mM DMSO STD plate, 15 µL or 5 µL was transferred into the remaining empty plate, and then 485 µL or 495 µL of DMSO was added to that plate to have a STD concentration of 300 µM. From the 300 µM DMSO STD plate, 5 µL was transferred into the remaining empty plate, and then 495 µL of a mixture of H2O and acetonitrile (1:1 in v/v) was added to that plate to have a final STD concentration of 3 µM. 200 µL of diluent was transferred to a new 96-well plate for LC-MS/MS analysis. The concentrations of the standard samples were changed according to the LC-MS signal response.
4. Procedure for sample analysis. The plate was placed into the well plate autosampler. The samples were evaluated by LC-MS/MS analysis.

The solubility values for Formula (A), Formula B, Formula (C), and select comparators are provided in Table 1, below.

TABLE 1

| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
|  | 1.9 | 11 | 4.2 | 282 (n = 2) | 42 (n = 1) |

Formula (A)

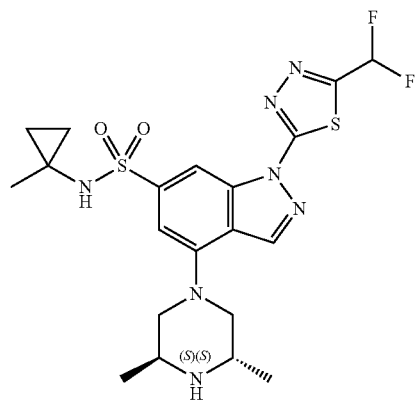

TABLE 1-continued
| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
| Formula (C) | 15 | 27 | 11 | 271 (n = 1) | 31 (n = 1) |
| Formula (B) | 51 | 89 | 32 | 261* (n = 1) | 41* (n = 1) |
| Example 115 from WO2016/097749 | >10000 | >10000 | >10000 | 29* (n = 1) | 24* (n = 1) |
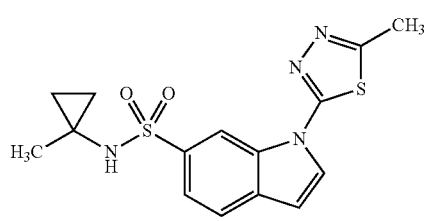

TABLE 1-continued

| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
| Example 38 from WO2021/055744 | 19 | 104 | 64 | 1.1* (n = 2) | 2.1* (n = 2) |
| Example 82 from WO2021/055744 | 39 | 146 | 75 | 2.1* (n = 2) | 5.6* (n = 2) |

TABLE 1-continued

| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
| Example 88 from WO2021/055744 | 76 | 184 | 137 | 3.4* (n = 1) | 8.0* (n = 1) |
| Example 89 from WO2021/055744 | 79 | 178 | 101 | <0.03* (n = 1) | <0.03* (n = 1) |
| Example 102 from WO2021/055744 | 201 | 1577 | 439 | 289* (n = 2) | 2.7* (n = 2) |

TABLE 1-continued
| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
| Example 24 from WO2021/055744 | 7.3 | 36 | 8.3 | 0.2* (n = 1) | 0.3* (n = 1) |
| 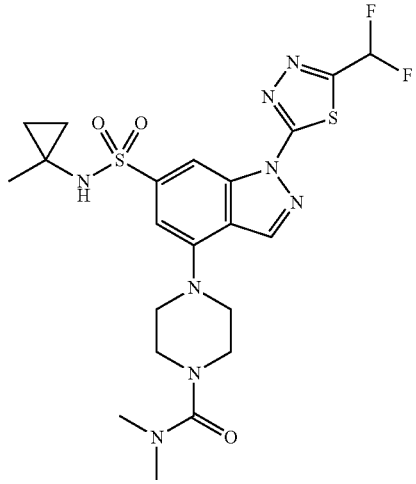 | 6.6 | 81 | 49 | 1.00* (n = 2) | 1.4* (n = 2) |
| Example 43 from WO2021/055744 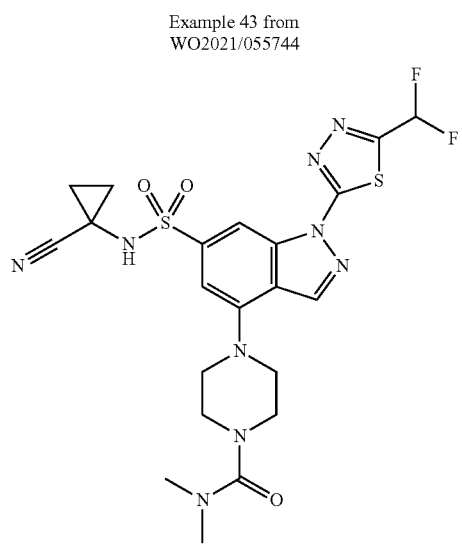 [SMILES: CC(C)C(=O)N1CCN(c2cc(S(=O)(=O)NC3(C#N)CC3)cc3c2cnn3-c2nnc(C(F)F)s2)CC1] | | | | | |

TABLE 1-continued

| Compound | TR-FRET EC50 (nM) | Cellular viability SNU601 EC50 (nM) | Cellular viability RMUGS EC50 (nM) | Solubility pH 2.0 (uM) | Kinetic Solubility pH 7.4 (uM) |
|---|---|---|---|---|---|
| Example 35 from WO2021/055744 | 9.9 | 84 | 60 | 7.2* (n = 1) | 14* (n = 1) |
| Example 83 from WO2021/055744 | 14 | 110 | 77 | 7.8* (n = 1) | 14* (n = 1) |

Data legend: Geometric mean (full dataset); *n <3 ("n" is number of runs)

Example 4

PARG Inhibition in PARP Inhibitor-Resistant and Platin-Resistant Cell Lines

Materials and Methods

Generation of PARP Inhibitor (PARPi) Acquired Resistant Cell Lines

Two cell lines were used to generate PARPi resistant lines: HCC1428 and MDA-MB-436. All cell lines were cultured in media as per manufacturer recommendations at 37° C. and 5% CO2. To generate the resistance cell lines, an IC50 concentration of niraparib, a PARP inhibitor, was added to each cell line and increased to IC90 in small increments over the course of 3-4 months until the cell lines adapted, developed resistance, and started proliferating in the presence of the high dose of niraparib. The cell lines were used for the studies disclosed in FIG. 1 and FIG. 2.

Cell Proliferation Assay

A panel of cell lines (as disclosed in Table 2) that show inherent resistance to PARP inhibitors were identified and the effect of Formula A was tested using the cellular proliferation assay along with the 2 acquired resistant cell lines (PARPi resistant lines: HCC1428 and MDA-MB-436). For the proliferation assay, the cell lines were plated in 96 well plates (Corning #3904) at density of 1000 cells/well. DMSO dissolved compound was added using the TECAN liquid dispenser to generate a 9-point dose curve with a 3-fold dilution and 10 uM starting, top concentration. After 5 population doublings, the cell lines were treated with 5 uM of Vybrant DyeCycle Green (Life Technologies #V35004) and incubated for 60 minutes. The DMSO and compound treated wells were then imaged using the Incucyte® S3 system to determine the nuclear counts. The counts were normalized to the DMSO treated wells and the IC50 was determined using the standard four parametric dose response equation in GraphPad Prism Software.

Patient Derived Cells Tested in a Cellular Viability Assay

Patient Derived Cells (PDC) from ovarian tissue with BRCA1/2 alterations and cisplatin resistance were identified. These cells were processed from solid tumor samples received after surgery/resection and 2-D cultured in selective media. For each PDC, upon reaching the required number of cells for the assay, the cells were detached using TrypLE and counted. Draq7 dye was added to the cells before plating to identify dead cells. The cells were plated in a 96 well plate (Greiner #655090) and incubated at 37° C. and 5% CO2 for 16-24h. A Tecan HP D300 digital dispenser was used to dispense Formula (A) in a 9-point dose curve and 3-fold dilution starting at 30 uM. 7 days post-incubation with the compound, the cells were fixed with 2% formaldehyde and stained with Hoechst. The plates were scanned using Nexcelom Celigo high content screening and the total cell count using Hoechst labeling and cell death using Draq7 fluorescence was analyzed. For all PDCs, the nuclear counts were normalized to the DMSO treated wells and the IC50 was determined using the standard four parametric dose response equation in GraphPad Prism Software. The cells generated were used for the study as disclosed in FIG. 3.

Results:

PARPi Inherent and Acquired Resistant Cell Lines are Sensitive to Formula A

Figure 2:
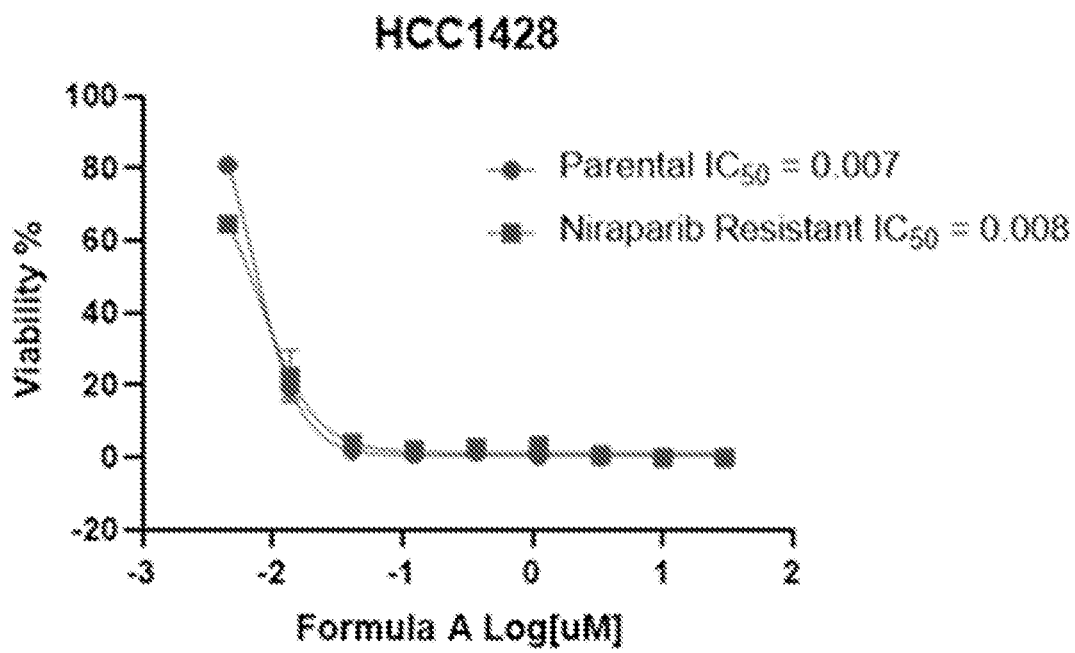
FIG. 2 plots percent viability of PARPi resistant HCC1428 cells as a function of the Log concentration of Formula A as described in Example 4. "Parental IC$_{50}$" refers to the IC$_{50}$ of Formula A before the cells developed PARPi resistance, while "Niraparib resistance IC$_{50}$" refers to the IC$_{50}$ of Formula A after the cells developed PARPi resistance.
Figure 3:
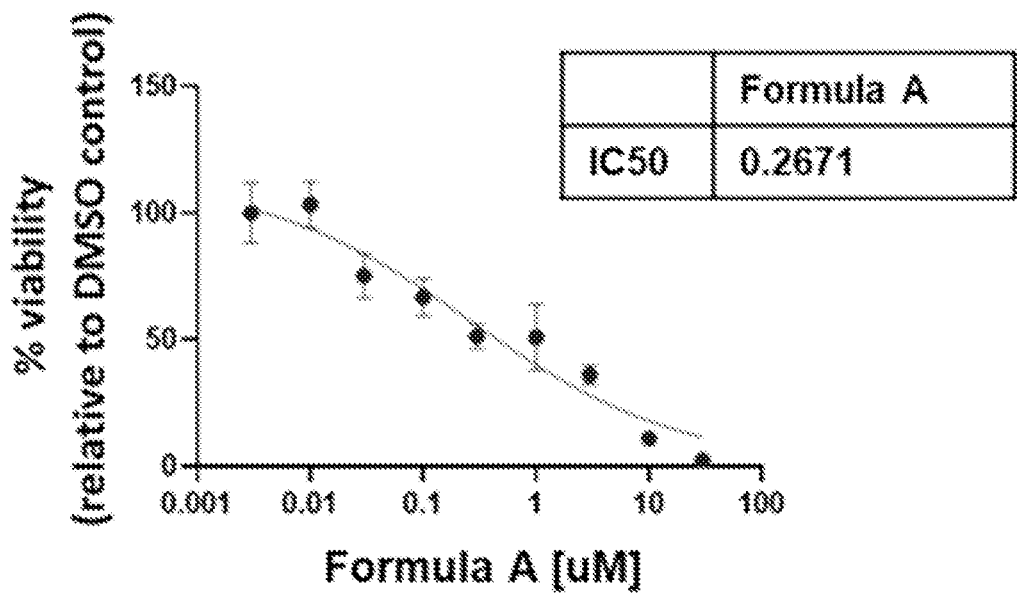
FIG. 3 plots patient derived cells (PDC) from ovarian tissue with BRCA1/2 alterations and cisplatin resistance as a function of the concentration of Formula A as described in Example 4.

The anti-proliferative effects of PARG inhibition on a panel of cancer cell lines that are inherently resistant to PARP inhibitors were tested using Formula A. Several cell lines that harbor BRCA1/2 loss of function alterations and are resistant to Niraparib showed sensitivity to Formula A (Table 2). Two breast cancer cell lines, MDA-MB-436 and HCC1428, with acquired resistance to PARPi were also tested in the proliferation assay. In MDA-MB-436, Formula A was 9 times more potent in the Niraparib resistant cell line (11.8 nM) compared to the parental cell line (103 nM) (FIG. 1). HCC1428 PARPi resistant cell line retained its sensitivity to Formula A with an IC50 of 8 nM (FIG. 2). Formula A was also tested in an ovarian Patient Derived Cell (PDC) model with BRCA1 mutation and cisplatin resistance. Formula A had an anti-proliferative effect on the cell line with an IC50 of 260 nM (FIG. 3).

TABLE 2

| Sensitivity of a panel of PARPi resistant cell lines to Formula (A) Cell line | Lineage | BRCA1/2 alteration | Formula A IC50 (uM) | Niraparib IC50 (uM) |
| --- | --- | --- | --- | --- |
| RMUG-S | Ovarian | BRCA1/2 | 0.008 | 2.7 |
| Kuramochi | Ovarian | BRCA2 | 0.009 | 1.3 |
| OVISE | Ovarian | BRCA2 | 0.05 | 0.68 |
| OVMANA | Ovarian | BRCA2 | 0.12 | 0.92 |
| HCC1569 | Breast | BRCA2 | 0.08 | 0.57 |
| CAL851 | Breast | BRCA2 | 0.1 | 0.89 |
| HCC1937 | Breast | BRCA1 | 0.22 | 2.27 |
| HCC1954 | Breast | BRCA1 | 0.37 | 17.6 |

Example 5

Patient-Derived Xenograft (PDX) Study

Female Athymic Nude—Foxn1$^{nu}$ mice with an established growing HBCx-34 tumor between 108 and 288 mm$^3$ were randomized into 2 treatment groups of 8 mice each, according to the groups listed in Table 3, tumor-bearing mice receive estrogen diluted in drinking water ((3-estradiol, 8.5 mg/l), from the date of tumor implant to the end of the study. In Table 3, the abbreviation "p.o." refers to oral administration, the abbreviation "QD" refers to administration once a day.

TABLE 3

| HBCx-34 tumor model study groups | | | |
| --- | --- | --- | --- |
| Group | Treatment | Dose regimen | Dose Vol (ml/kg) |
| 1 | Vehicle | p.o., QD × 45 | 10 |
| 2 | Formula A | 100 mg/kg, p.o., QD × 45 | 10 |

Figure 4:
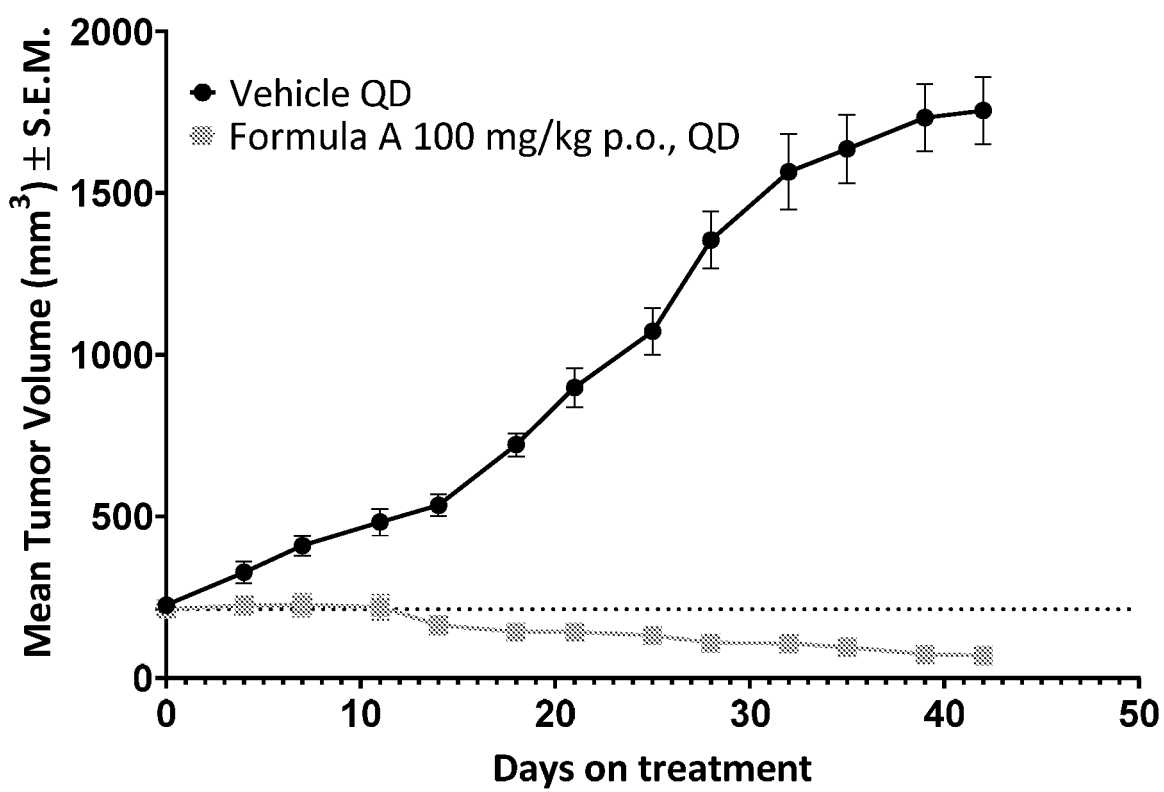
FIG. 4: Shows Patient-derived xenograft (PDX) study with HBCx-34 (Formula A).

Tumors were measured and mice were weighed twice per week during the experimental period. The tumor volume (mm$^3$) was estimated using the formula: tumor volume (TV)=a×b2/2, where "a" and "b" were the long and the short diameter of a tumor, respectively. The TVs were used to calculate tumor growth inhibition (TGI, an indicator of antitumor activity) using the formula TGI %: (1−{T/T0/Ct/C0}/1−{C0/Ct})×100 where Tt=median tumor volume of treated at time t, T0=median tumor volume of treated at time 0, Ct=median tumor volume of control at time t and C0=median tumor volume of control at time 0. Formula A administered at 100 mg/kg resulted in a robust and statistically significant anti-tumor response, with all mice achieving partial regression. A summary of the results are shown in Table 4 (FIG. 4). Tumor regression represents tumor volume less than the initial tumor volume at D0.

TABLE 4

| Tumor growth inhibition compared with vehicle group on Day 45. | | |
| --- | --- | --- |
| Formula A dose | TGI (%) D45 | p value, treated vs. Vehicle |
| 100 mg/kg QD | 110 | p < 0.0001 |

REFERENCES

[1] Ame, J. C., E. Fouquerel, L. R. Gauthier, D. Biard, F. D. Boussin, F. Dantzer, G. de Murcia and V. Schreiber (2009). "Radiation-induced mitotic catastrophe in PARG-deficient cells." J Cell Sci 122(Pt 12): 1990-2002.

[2] Barber, L. J., S. Sandhu, L. Chen, J. Campbell, I. Kozarewa, K. Fenwick, I. Assiotis, D. N. Rodrigues, J. S. Reis Filho, V. Moreno, J. Mateo, L. R. Molife, J. De Bono, S. Kaye, C. J. Lord and A. Ashworth (2013). "Secondary mutations in BRCA2 associated with clinical resistance to a PARP inhibitor." J Pathol 229(3): 422-429.

[3] Blenn, C., P. Wyrsch and F. R. Althaus (2011). "The ups and downs of tannins as inhibitors of poly(ADP-ribose) glycohydrolase." Molecules 16(2): 1854-1877.

[4] Caiafa, P., T. Guastafierro and M. Zampieri (2009). "Epigenetics: poly(ADP-ribosyl)ation of PARP-1 regulates genomic methylation patterns." FASEB J 23(3): 672-678.

[5] Curtin, N. J. and C. Szabo (2013). "Therapeutic applications of PARP inhibitors: anticancer therapy and beyond." Mol Aspects Med 34(6): 1217-1256.

[6] Dahl, M., V. Maturi, P. Lonn, P. Papoutsoglou, A. Zieba, M. Vanlandewijck, L. P. van der Heide, Y. Watanabe, O. Soderberg, M. O. Hottiger, C. H. Heldin and A. Moustakas (2014). "Fine-tuning of Smad protein function by poly(ADP-ribose) polymerases and poly(ADP-ribose) glycohydrolase during transforming growth factor beta signaling." PLoS One 9(8): e103651.

[7] Drost, R. and J. Jonkers (2014). "Opportunities and hurdles in the treatment of BRCA1-related breast cancer." Oncogene 33(29): 3753-3763.

[8] Erdelyi, K., P. Bai, I. Kovacs, E. Szabo, G. Mocsar, A. Kakuk, C. Szabo, P. Gergely and L. Virag (2009). "Dual role of poly(ADP-ribose) glycohydrolase in the regulation of cell death in oxidatively stressed A549 cells." FASEB J 23(10): 3553-3563.

[9] Fathers, C., R. M. Drayton, S. Solovieva and H. E. Bryant (2012). "Inhibition of poly(ADP-ribose) glycohydrolase (PARG) specifically kills BRCA2-deficient tumor cells." Cell Cycle 11(5): 990-997.

[10] Fisher, A. E., H. Hochegger, S. Takeda and K. W. Caldecott (2007). "Poly(ADP-ribose) polymerase 1 accelerates single-strand break repair in concert with poly (ADP-ribose) glycohydrolase." Mol Cell Biol 27(15): 5597-5605.

[11] Frizzell, K. M., M. J. Gamble, J. G. Berrocal, T. Zhang, R. Krishnakumar, Y. Cen, A. A. Sauve and W. L. Kraus (2009). "Global analysis of transcriptional regulation by poly(ADP-ribose) polymerase-1 and poly(ADP-ribose) glycohydrolase in MCF-7 human breast cancer cells." J Biol Chem 284(49): 33926-33938.

[12] Fujihara, H., H. Ogino, D. Maeda, H. Shirai, T. Nozaki, N. Kamada, K. Jishage, S. Tanuma, T. Takato, T. Ochiya, T. Sugimura and M. Masutani (2009). "Poly(ADP-ribose) Glycohydrolase deficiency sensitizes mouse ES cells to DNA damaging agents." Curr Cancer Drug Targets 9(8): 953-962.

[13] Guastafierro, T., A. Catizone, R. Calabrese, M. Zampieri, O. Martella, M. G. Bacalini, A. Reale, M. Di Girolamo, M. Miccheli, D. Farrar, E. Klenova, F. Ciccarone and P. Caiafa (2013). "ADP-ribose polymer depletion leads to nuclear Ctcf re-localization and chromatin rearrangement(1)." Biochem J 449(3): 623-630.

[14] Ji, Y. and A. V. Tulin (2009). "Poly(ADP-ribosyl)ation of heterogeneous nuclear ribonucleoproteins modulates splicing." Nucleic Acids Res 37(11): 3501-3513.

[15] Le May, N., I. Iltis, J. C. Ame, A. Zhovmer, D. Biard, J. M. Egly, V. Schreiber and F. Coin (2012). "Poly (ADP-ribose) glycohydrolase regulates retinoic acid receptor-mediated gene expression." Mol Cell 48(5): 785-798.

[16] Mashimo, M., J. Kato and J. Moss (2014). "Structure and function of the ARH family of ADP-ribosyl-acceptor hydrolases." DNA Repair (Amst).

[17] Mortusewicz, O., E. Fouquerel, J. C. Ame, H. Leonhardt and V. Schreiber (2011). "PARG is recruited to DNA damage sites through poly(ADP-ribose)- and PCNA-dependent mechanisms." Nucleic Acids Res 39(12): 5045-5056.

[18] Nakadate, Y., Y. Kodera, Y. Kitamura, T. Tachibana, T. Tamura and F. Koizumi (2013). "Silencing of poly(ADP-ribose) glycohydrolase sensitizes lung cancer cells to radiation through the abrogation of DNA damage checkpoint." Biochem Biophys Res Commun 441(4): 793-798.

[19] Shirai, H., H. Fujimori, A. Gunji, D. Maeda, T. Hirai, A. R. Poetsch, H. Harada, T. Yoshida, K. Sasai, R. Okayasu and M. Masutani (2013). "Parg deficiency confers radio-sensitization through enhanced cell death in mouse ES cells exposed to various forms of ionizing radiation." Biochem Biophys Res Commun 435(1): 100-106.

[20] Shirai, H., A. R. Poetsch, A. Gunji, D. Maeda, H. Fujimori, H. Fujihara, T. Yoshida, H. Ogino and M. Masutani (2013). "PARG dysfunction enhances DNA double strand break formation in S-phase after alkylation DNA damage and augments different cell death pathways." Cell Death Dis 4: e656.

[21] Sun, Y., T. Zhang, B. Wang, H. Li and P. Li (2012). "Tannic acid, an inhibitor of poly(ADP-ribose) glycohydrolase, sensitizes ovarian carcinoma cells to cisplatin." Anticancer Drugs 23(9): 979-990.

[22] Zhou, Y., X. Feng and D. W. Koh (2010). "Enhanced DNA accessibility and increased DNA damage induced by the absence of poly(ADP-ribose) hydrolysis." Biochemistry 49(34): 7360-7366.

[23] Zhou, Y., X. Feng and D. W. Koh (2011). "Synergistic cytotoxicity of N-methyl-N'-nitro-N-nitrosoguanidine and absence of poly(ADP-ribose) glycohydrolase involves chromatin decondensation." Int J Oncol 39(1): 121-127.

[24] Milbury C A, Creeden J, Yip W K, Smith D L, Pattani V, Maxwell K, Sawchyn B, Gjoerup O, Meng W, Skoletsky J, Concepcion A D, Tang Y, Bai X, Dewal N, Ma P, Bailey S T, Thornton J, Pavlick D C, Frampton G N, Lieber D, White J, Burns C, Vietz C (2022) "Clinical and analytical validation of FoundationOne®CDx, a comprehensive genomic profiling assay for solid tumors." PLOS ONE 17(3): e0264138. https://doi.org/10.1371/journal.pone.0264138

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A compound of Formula (I):

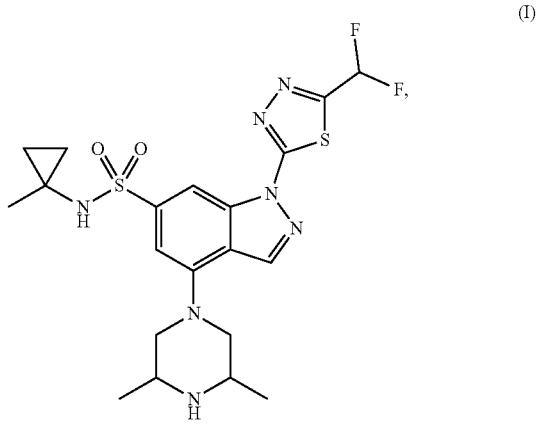 [SMILES: CC1CN(c2cc(S(=O)(=O)NC3(C)CC3)cc3c2cnn3-c2nnc(C(F)F)s2)CC(C)N1]

or a pharmaceutically acceptable salt thereof.

2. A compound of Formula (A):

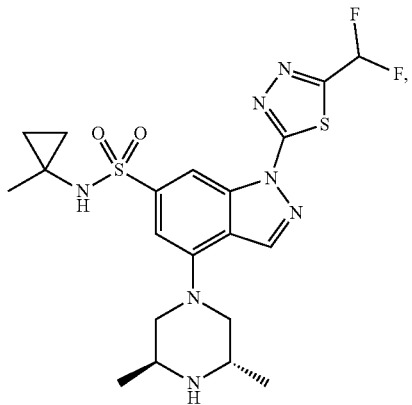

or a pharmaceutically acceptable salt thereof.

3. The compound of claim 1, represented by Formula (I):

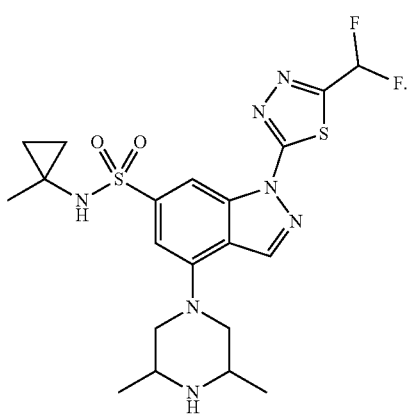

4. The compound of claim 2, represented by Formula (A):

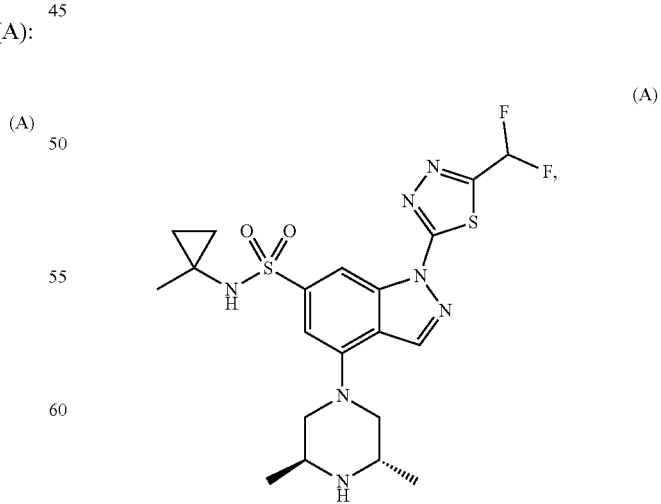

5. A pharmaceutical composition comprising a compound of Formula (I):

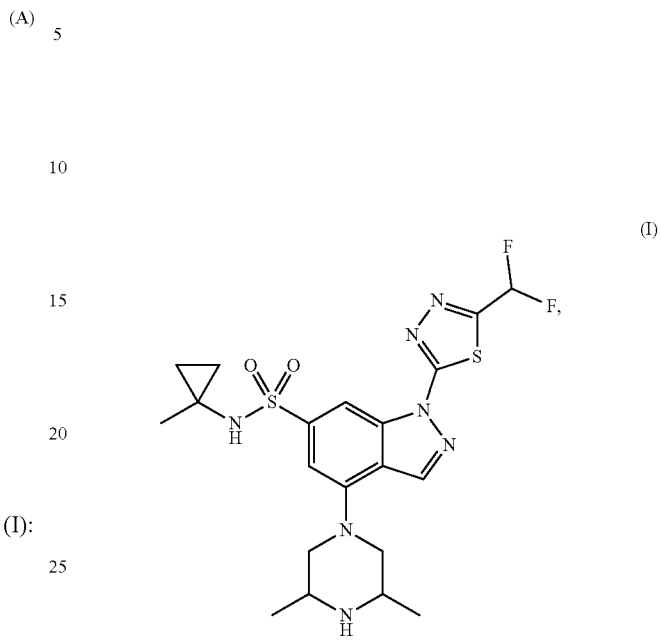

or a pharmaceutically acceptable salt thereof, and a pharmaceutically acceptable excipient.

6. A pharmaceutical composition comprising a compound of Formula (A):

or a pharmaceutically acceptable salt thereof, and a pharmaceutically acceptable excipient.

7. The compound of claim 1, represented by Formula (B):

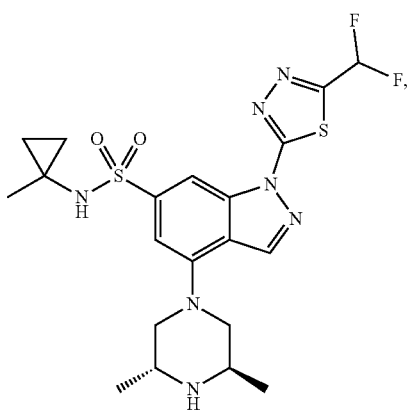

(B)

or a pharmaceutically acceptable salt thereof.

8. The compound of claim 7, represented by Formula (B):

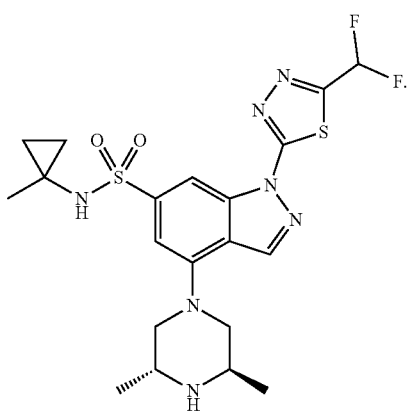

(B)

9. A pharmaceutical composition comprising a compound or a pharmaceutically acceptable salt thereof of claim 7, and a pharmaceutically acceptable excipient.

10. The compound of claim 1, represented by Formula (C):

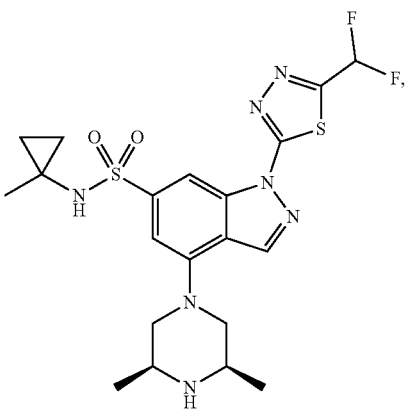

(C)

or a pharmaceutically acceptable salt thereof.

11. The compound of claim 10, represented by Formula (C):

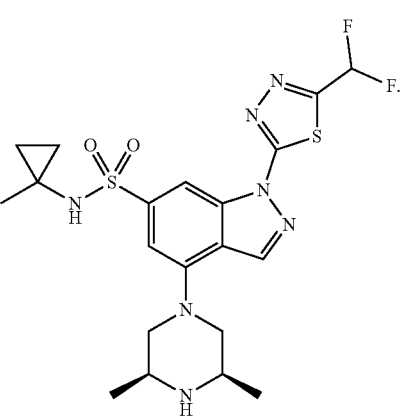

(C)

12. A pharmaceutical composition comprising a compound or a pharmaceutically acceptable salt thereof of claim 10, and a pharmaceutically acceptable excipient.

* * * * *